United States Patent
Agresta

(10) Patent No.: US 11,419,859 B2
(45) Date of Patent: Aug. 23, 2022

(54) COMBINATION THERAPY FOR TREATING MALIGNANCIES

(71) Applicant: Servier Pharmaceuticals LLC, Boston, MA (US)

(72) Inventor: Samuel V. Agresta, Lexington, MA (US)

(73) Assignee: SERVIER PHARMACEUTICALS LLC, Boston, MA (US)

( * ) Notice: Subject to any disclaimer, the term of this patent is extended or adjusted under 35 U.S.C. 154(b) by 145 days.

(21) Appl. No.: 15/767,813

(22) PCT Filed: Oct. 14, 2016

(86) PCT No.: PCT/US2016/057036
§ 371 (c)(1),
(2) Date: Apr. 12, 2018

(87) PCT Pub. No.: WO2017/066566
PCT Pub. Date: Apr. 20, 2017

(65) Prior Publication Data
US 2018/0303808 A1 Oct. 25, 2018

Related U.S. Application Data

(60) Provisional application No. 62/255,253, filed on Nov. 13, 2015, provisional application No. 62/242,267, filed on Oct. 15, 2015.

(51) Int. Cl.
| | |
|---|---|
| *A61K 31/444* | (2006.01) |
| *A61K 31/704* | (2006.01) |
| *A61K 31/7068* | (2006.01) |
| *C07H 19/09* | (2006.01) |
| *C07H 15/252* | (2006.01) |
| *C07D 403/14* | (2006.01) |
| *A61P 35/02* | (2006.01) |
| *A61K 31/136* | (2006.01) |
| *A61K 31/7048* | (2006.01) |

(52) U.S. Cl.
CPC .......... *A61K 31/444* (2013.01); *A61K 31/136* (2013.01); *A61K 31/704* (2013.01); *A61K 31/7048* (2013.01); *A61K 31/7068* (2013.01); *A61P 35/02* (2018.01); *C07D 403/14* (2013.01); *C07H 15/252* (2013.01); *C07H 19/09* (2013.01)

(58) Field of Classification Search
CPC ....... C07H 15/252; C07H 19/09; A61P 35/02; A61K 31/7068; A61K 31/444; A61K 31/704; A61K 31/7048; A61K 31/136
See application file for complete search history.

(56) References Cited

U.S. PATENT DOCUMENTS

| | | | |
|---|---|---|---|
| 2,390,529 | A | 12/1945 | Friedheim |
| 3,755,322 | A | 8/1973 | Winter et al. |
| 3,867,383 | A | 2/1975 | Winter |
| 4,084,053 | A | 4/1978 | Desai et al. |
| 5,021,421 | A | 6/1991 | Hino et al. |
| 5,489,591 | A | 2/1996 | Kobayashi et al. |
| 5,807,876 | A | 9/1998 | Armistead et al. |
| 5,834,485 | A | 11/1998 | Dyke et al. |
| 5,965,559 | A | 10/1999 | Faull et al. |
| 5,965,569 | A | 10/1999 | Camps Garcia et al. |
| 5,984,882 | A | 11/1999 | Rosenschein et al. |
| 6,262,113 | B1 | 7/2001 | Widdowson et al. |
| 6,274,620 | B1 | 8/2001 | Labrecque et al. |
| 6,313,127 | B1 | 11/2001 | Waterson et al. |
| 6,399,358 | B1 | 6/2002 | Williams et al. |
| 6,576,235 | B1 | 6/2003 | Williams et al. |
| 6,723,730 | B2 | 4/2004 | Bakthavatchalam et al. |
| 6,783,965 | B1 | 8/2004 | Sherman et al. |
| 6,979,675 | B2 | 12/2005 | Tidmarsh |
| 7,173,025 | B1 | 2/2007 | Stocker et al. |
| 7,858,782 | B2 | 12/2010 | Tao et al. |
| 8,133,900 | B2 | 3/2012 | Hood et al. |
| 8,257,741 | B2 | 9/2012 | Curatolo et al. |
| 8,263,128 | B2 | 9/2012 | Curatolo et al. |
| 8,337,899 | B2 | 12/2012 | Curatolo et al. |
| 8,367,118 | B2 | 2/2013 | Curatolo et al. |
| 8,431,159 | B2 | 4/2013 | Curatolo et al. |
| 8,465,673 | B2 | 6/2013 | Yasuda et al. |
| 9,474,779 | B2* | 10/2016 | Lemieux .............. C07D 417/04 |
| 9,850,277 | B2* | 12/2017 | Popovici-Muller ......................... C07D 403/04 |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Silverman, "THe ORganic Chemistry of Drug Design and Drug Action" published by Academic Press, pp. 19-21 and 352-397 (Year: 1992).*

(Continued)

*Primary Examiner* — Eric Olson
(74) *Attorney, Agent, or Firm* — Goodwin Procter LLP

(57) ABSTRACT

Provided are methods and compositions for treating acute myelogenous leukemia (AML) in patients carrying an IDH1 mutation using an inhibitor of a mutant IDH1 enzyme, (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide in combination with cytarabine and doxorubicin or idarubicin as an induction therapy and either cytarabine or a combination of combination of mitoxantrone and etoposide as consolidation therapy.

22 Claims, 6 Drawing Sheets

(56) References Cited

U.S. PATENT DOCUMENTS

| | | | |
|---|---|---|---|
| 9,968,595 B2 * | 5/2018 | Gu | A61K 9/2054 |
| 10,111,882 B2 | 10/2018 | Abella et al. | |
| 10,449,184 B2 | 10/2019 | Gu | |
| 2002/0049310 A1 | 4/2002 | Tateishi et al. | |
| 2002/0188027 A1 | 12/2002 | Robinson et al. | |
| 2003/0095958 A1 | 5/2003 | Bhisetti et al. | |
| 2003/0109527 A1 | 6/2003 | Jin et al. | |
| 2003/0207882 A1 | 11/2003 | Stocker et al. | |
| 2003/0213405 A1 | 11/2003 | Harada et al. | |
| 2004/0067234 A1 | 4/2004 | Einat et al. | |
| 2004/0248221 A1 | 12/2004 | Stockwell | |
| 2005/0261268 A1 | 11/2005 | Arnost et al. | |
| 2006/0084645 A1 | 4/2006 | Pal et al. | |
| 2006/0281122 A1 | 12/2006 | Bryant et al. | |
| 2007/0244088 A1 | 10/2007 | Brickmann et al. | |
| 2008/0132490 A1 | 6/2008 | Bergman et al. | |
| 2008/0300208 A1 | 12/2008 | Einat et al. | |
| 2009/0093526 A1 | 4/2009 | Miller et al. | |
| 2009/0163508 A1 | 6/2009 | Kori et al. | |
| 2009/0163545 A1 | 6/2009 | Goldfarb | |
| 2009/0281089 A1 | 11/2009 | Gunzner et al. | |
| 2009/0286752 A1 | 11/2009 | Etter et al. | |
| 2010/0129350 A1 | 5/2010 | Zacharie et al. | |
| 2010/0144722 A1 | 6/2010 | Alexander et al. | |
| 2010/0273808 A1 | 10/2010 | Armitage et al. | |
| 2010/0331307 A1 | 12/2010 | Salituro et al. | |
| 2011/0073007 A1 | 3/2011 | Yasuda et al. | |
| 2011/0086088 A1 | 4/2011 | Berry | |
| 2011/0288065 A1 | 11/2011 | Fujihara et al. | |
| 2012/0121515 A1 | 5/2012 | Dang et al. | |
| 2012/0129865 A1 | 5/2012 | Wang et al. | |
| 2012/0164143 A1 | 6/2012 | Teeling et al. | |
| 2012/0202818 A1 | 8/2012 | Tao et al. | |
| 2012/0238576 A1 | 9/2012 | Tao et al. | |
| 2012/0277233 A1 | 11/2012 | Tao et al. | |
| 2013/0035329 A1 | 2/2013 | Saunders et al. | |
| 2013/0109643 A1 | 5/2013 | Riggins et al. | |
| 2013/0183281 A1 | 7/2013 | Su et al. | |
| 2013/0184222 A1 | 7/2013 | Popovici-Muller et al. | |
| 2013/0190249 A1 | 7/2013 | Lemieux et al. | |
| 2013/0190287 A1 | 7/2013 | Cianchetta et al. | |
| 2013/0197106 A1 | 8/2013 | Fantin et al. | |
| 2014/0094503 A1 | 4/2014 | Ma et al. | |
| 2014/0187435 A1 | 7/2014 | Dang et al. | |
| 2014/0206673 A1 | 7/2014 | Cao et al. | |
| 2014/0213580 A1 | 7/2014 | Cao et al. | |
| 2015/0018328 A1 | 1/2015 | Konteatis et al. | |
| 2015/0031627 A1 | 1/2015 | Lemieux et al. | |
| 2015/0031641 A1 | 1/2015 | Levine et al. | |
| 2015/0044716 A1 | 2/2015 | Balss et al. | |
| 2015/0087600 A1 | 3/2015 | Popovici-Muller et al. | |
| 2015/0240286 A1 | 8/2015 | Dang et al. | |
| 2015/0299115 A1 | 10/2015 | Popovici-Muller et al. | |
| 2016/0130298 A1 | 5/2016 | Lemieux et al. | |
| 2016/0264621 A1 | 9/2016 | Popovici-Muller et al. | |
| 2016/0304556 A1 | 10/2016 | Popovici-Muller et al. | |
| 2017/0007661 A1 | 1/2017 | Gu | |
| 2017/0014396 A1 | 1/2017 | Gu | |
| 2017/0015703 A1 | 1/2017 | Popovici-Muller et al. | |
| 2017/0057994 A1 | 3/2017 | Lemieux et al. | |
| 2018/0296583 A1 | 10/2018 | Agresta et al. | |
| 2018/0303840 A1 | 10/2018 | Chopra et al. | |
| 2018/0325880 A1 | 11/2018 | Gu | |
| 2019/0046512 A1 | 2/2019 | Amatangelo et al. | |
| 2019/0336487 A1 | 11/2019 | Gu | |

FOREIGN PATENT DOCUMENTS

| | | |
|---|---|---|
| CN | 102659765 A | 9/2012 |
| CN | 103097340 A | 5/2013 |
| DE | 2263878 A1 | 7/1973 |
| DE | 3314663 A1 | 10/1983 |
| DE | 3512630 A1 | 10/1986 |
| EP | 0022958 A1 | 1/1981 |
| EP | 0384228 A1 | 8/1990 |
| EP | 0385237 A2 | 9/1990 |
| EP | 901786 A2 | 3/1999 |
| EP | 0945446 A1 | 9/1999 |
| EP | 1391487 A2 | 2/2004 |
| EP | 1886673 A2 | 2/2008 |
| FR | 2735127 A1 | 12/1996 |
| GB | 1033266 A | 6/1966 |
| JP | H04099768 A | 3/1992 |
| JP | H05140126 A | 6/1993 |
| JP | H09291034 A | 11/1997 |
| JP | H11158073 A | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| TW | 201028381 A | 8/2010 |
| WO | 1996030343 A1 | 10/1996 |
| WO | 9728128 | 8/1997 |
| WO | 9728129 | 8/1997 |
| WO | 1997044322 A1 | 11/1997 |
| WO | 9932463 A1 | 7/1999 |
| WO | 00002864 A1 | 1/2000 |
| WO | 2001016097 A1 | 3/2001 |
| WO | 2001019788 A2 | 3/2001 |
| WO | 2001019798 A2 | 3/2001 |
| WO | 0147897 A1 | 7/2001 |
| WO | 2001064642 A2 | 9/2001 |
| WO | 2001064643 A2 | 9/2001 |
| WO | 2002100822 A1 | 12/2002 |
| WO | 2002102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A1 | 12/2005 |
| WO | 2006034341 A2 | 3/2006 |
| WO | 2006038594 A1 | 4/2006 |
| WO | 2006070198 A1 | 7/2006 |
| WO | 2006079791 A1 | 8/2006 |
| WO | 2006/110761 A2 | 10/2006 |
| WO | 2007003934 A2 | 1/2007 |
| WO | 2007023186 A1 | 3/2007 |
| WO | 2008036835 A2 | 3/2008 |
| WO | 2008050168 A1 | 5/2008 |
| WO | 2008050186 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009013126 A1 | 1/2009 |
| WO | 2009015254 A1 | 1/2009 |
| WO | 2009016410 A2 | 2/2009 |
| WO | 2009118567 A2 | 10/2009 |
| WO | 2009126863 A2 | 10/2009 |
| WO | 2009150248 A1 | 12/2009 |
| WO | 2010007756 A1 | 1/2010 |
| WO | 2010028099 A1 | 3/2010 |
| WO | 2010105243 A1 | 9/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 201105210 A1 | 1/2011 |
| WO | 2011002817 A1 | 1/2011 |
| WO | 2011/027249 A2 | 3/2011 |
| WO | 2011032169 A2 | 3/2011 |
| WO | 2011047432 A1 | 4/2011 |

(56) References Cited

FOREIGN PATENT DOCUMENTS

| WO | 2011050210 A1 | 4/2011 |
|---|---|---|
| WO | 2011072174 A1 | 6/2011 |
| WO | 2012006506 A1 | 1/2012 |
| WO | 2012009678 A1 | 1/2012 |
| WO | 2012074999 A1 | 6/2012 |
| WO | 2012092442 A1 | 7/2012 |
| WO | 2012151452 A1 | 11/2012 |
| WO | 2012160034 A1 | 11/2012 |
| WO | 2012171337 A1 | 12/2012 |
| WO | 2012171506 A1 | 12/2012 |
| WO | 2012173682 A2 | 12/2012 |
| WO | 2013004332 A1 | 1/2013 |
| WO | 2013007708 A1 | 1/2013 |
| WO | 2013016206 A1 | 1/2013 |
| WO | 2013102431 A1 | 7/2013 |
| WO | 2013107291 A1 | 7/2013 |
| WO | 2013107405 A1 | 7/2013 |
| WO | 2013133367 A1 | 9/2013 |
| WO | 2014015422 A1 | 1/2014 |
| WO | 2015/003360 A2 | 1/2015 |
| WO | 2015127172 A1 | 8/2015 |
| WO | 2015127173 A1 | 8/2015 |
| WO | 2015138837 A1 | 9/2015 |
| WO | 2015138839 A1 | 9/2015 |
| WO | 2017066566 A1 | 4/2017 |
| WO | 2017066571 A1 | 4/2017 |
| WO | 2017096309 A1 | 6/2017 |
| WO | 2017146795 A1 | 8/2017 |

OTHER PUBLICATIONS

Lieberman et al., Pharmaceutical Dosage Forms, vol. 2 published by Marcel Dekker, INC, pp. 462-472 (Year: 1990).*
Braga et al., "Making Crystals from Crystals: a green route to crystal engineering and polymorphism" Chem Commun 2005 pp. 3635-3645 (Year: 2005).*
Jain et al., "Polymorphism in Pharmacy" Indian Drugs vol. 23 No. 6 pp. 315-329 (Year: 1986).*
Vippagunta et al., "Crystalline Solids" Advanced Drug Delivery Reviews vol. 48 pp. 3-26 (Year: 2001).*
Tefferi et al.., "Going Beyond 7+3 Regimens in the treatmetn of Adult Acute Myeloid Leukemia" Journal of Clinical Oncology vol. 30 No. 20 pp. 2425-2428 (Year: 2012).*
Stein et al., "Ivosedenib or enasidenib combined with intensive chemotherapy in patients with newly diagnosed AML: a phase 1 study" Blood vol. 137 No. 13 pp. 1792-1803 (Year: 2021).*
Serve et al., "Sorafenib in Combination with Intensive Chemotehrapy in Elderly Patients with Acute Myeloid Leukemia: Results from a Randomized, Placebo-Controlled Trial" Journal of Clinical Oncology vol. 31 No. 26 pp. 3110-3119 (Year: 2013).*
Domber et al., "An update of current treatments for adult acute myeloid leukemia" Blood vol. 127 No. 1 pp. 53-61 (Year: 2016).*
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]".
STN Registry, L23 Answer 2 of 3 (CAS No. 1032450-21-7), Database: ASINEX Ltd.,Entered STN: Jul. 3, 2008 (Jul. 3, 2008).

STN Registry. L23 Answer 1 of 3 (CAS No. 1038821-72-5),Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-1-piperazinyl)carbonyl]phenyl]".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-1-piperazinyl]carbonyl]phenyl]".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-1-piperazinyl]carbonyl]phenyl]".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-[{4-(tetrahydro-2-furanyl)methyl]-1-piperazinyl]carbonyl]phenyl],".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]".
STN Tokyo, Registry No. 878956-06-0, Entered STN on Apr. 2, 2006, Chemical Abstracts Index Name "1,4-Benzodioxin-6-sulfonamide, N-[4-[[4-(cyclopropylcarbonyl)-1-piperazinyl]carbonyl]phenyl]-2,3-dihydro".
STN Tokyo, Registry No. 920679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]".
STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro".
STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]".
STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]".
STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]".
STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-1-piperazinyl]carbonyl]phenyl]".

(56) References Cited

OTHER PUBLICATIONS

STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]".

STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]".

STN Tokyo, Registry No. 941220-77-5, Entered STN on Jul. 4, 2007, Chemical Abstracts Index Name "2H-1, 5-Benzodioxepin 7-sulfonamide, 3,4-dihydro N-[4-[(4-methyl-1-piperazinyl)carbonyl]phenyl]".

Struys et al., Investigations by mass isotopomer analysis of the formation of D-2-hydroxyglutarate by cultured lymphoblasts from two patients with D-2-hydroxyglutaric aciduria, FEES letters 92004 vol. 557, pp. 115-120.

Struys et al. "Mutations in the D-2-hydroxyglutarate dehydrogenase gene cause D-2-hydroxyglutaric aciduria" American Journal of Human Genetics, 2005. 76:358-360.

Struys, EA. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.

Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.

The radiation fact sheet published by the National Cancer Institute, http://www.cancer.gov/about-cancer/treatment/types/radiation-therapy/radiation-fact-sheet, reviewed Jun. 30, 2010.

Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.

Van Schaftingen et al. "L-2-Hydroglutaric aciduria, a disorder of metabolite repair" J Inherit. Metab. Dis. (2009) vol. 32, pp. 135-142.

Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.

Wang et al. "A novel ligand N,N?-di(2-pyridyl)-2,4-diamino-6-phenyl-1,3,5-triazine (dpdapt) and its complexes: [Cu(dpdapt)Cl2] and [Cu(dpdapt)(NO3)(H2O)] · NO3 · H2O" Polyhedron, 2006. vol. 25, Issue 1. pp. 195-202.

Ward, Patrick S, "The Common Feature of Leukemia-Associated IDH1 and IDH2 Mutations is a Neomorphic Enzyme Activity Converting [alpha]-Ketoglutarate to 2-Hydroxyglutarate" Cancer cell, vol. 17,Nr:3,pp. 225-234, 2010.

Watanabe et al., "IDH1 Mutations are Early Events in the Development of Astrocytomas and Oligodendrogliomas". American Journal of Pathology, Apr. 2009 (published online Feb. 26, 2009), vol. 174, No. 4, pp. 1149-1153 Abstract, p. 1150, col. 1.

Yan et al., "IDH1 and IDH2 Mutations in Gliomas" The New England Journal of Medicine, 79 Feb. 18-22, 2009, vol. 360, No. 8, pp. 765-773.

Yrjola et al., "Discovery of novel cannabinoid receptor ligands by a virtual screening approach: Further development of 2,4,6-trisubstituted 1,3,5-triazines as CB2 agonists," European Journal of Pharmaceutical Sciences (2013) vol. 48, pp. 9-20.

Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.

Zheng et al. "Synthesis and antitumor evaluation of a novel series of triaminotriazine derivatives" Bioorganic & Medicinal Chemistry (2007) vol. 15, pp. 1815-1827.

Zuo et al. "Synthesis of 4-methyl-1,2,3-thiadiazole derivatives via ugi reaction and their biological activities," Journal of Agricultural and Food Chemistry, 2010, 58(5): 2755-2762.

Aghili et al. "Hydroxyglutaric aciduria and malignant brain tumor: a case report and literature review", Journal of Neuroncology, 2008. 91:233-236.

Amary et al. "Ollier disease and Maffucci syndrome are caused by somatic mosiac mutations of IDH1 and IDH2," Mature Genetics Letters, 2011, 43(12):1262-1266.

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.

Balss, "Analysis of the IDH1 codon 132 mutation in brain tumors", Acata Neuropathol (2008) vol. 116, pp. 597-602.

Benner et al, "Evolution, language and analogy in functional genomics", Trends in Genetics (2001) vol. 17, pp. 414-418.

Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.

Bleeker et al., "IDH1 mutations at residue p. R132 (IDH1 (R132)) occur frequently in high-grade 18-22 gliomas but not in other solid tumors." Hum Mutal., Jan. 2009, vol. 30, No. 1, pp. 7-11.

Braun et al. "Triazine-based polymers: 4. MALDI-MS of triazine-based polyamines" Polymer (1996) vol. 37, No. 5, pp. 777-783.

Burger et al. "Nuclear substituted 3,4-dihydroxyphenethylamines and related derivatives," Journal of American Chemical Society, 1956, 78(17):4419-4422.

Cairns et al. "Oncogenic Isocitrate Dehydrogenase Mutations: Mechanisms, Models, and Clinical Opportunities" Cancer Discovery (2013) vol. 3, Iss 7, pp. 730-741.

Cecil Textbook of Medicine, edited by Bennet, J.C., and Plum F., 20th edition, vol. 1, 1004-1010, 1996.

Chan et al. "Multi-domain hydrogen-bond forming metal chelates: X-ray crystal structuresof dicyclopalladated 2,3-bis[6-(2-amino-4-phenylamino-1 ,3,5-triazinyl)]pyrazine(H2L) [Pd2Br2L] and 2,6-bis[6-(2-amino-4-phenylamino-1,3,5-triazinylium)] -pyridine dichloride" Chemical Communications (1996) No. 1, pp. 81-83.

Chapman et al. "Substituted aminopyrimidine protein kinase B (PknB) inhibitorsshow activity against Mycobacterium tuberculosis" Bioorganic & Medicinal Chemistry Letters (2012) vol. 22, pp. 3349-3353.

Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, p. 10044-10048.

Cocco et al. "Synthesis of Triflouromethylated Pyridinecarbonitriles" Journal of Heterocyclic Chemistry, 1995. vol. 32 pp. 543-545.

Dang et al., "Cancer-associated IDH1 mutations produce 2-hydroxyglutarate." Nature, 10 29-32 Dec. 2009, vol. 462, No. 7274, pp. 739-744.

Dang et al. "IDH Mutations in Glioma and Acute Myeloid Leukemia" Trends in Molecular Medicine (2010) vol. 16, No. 9, pp. 387-397.

Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes (2011), 64(4), 544-550 Coden: KZARF3; ISSN 1561-4190, 2011.

Database CA [Online] Chemical Abstracts Service. Columbus.Ohio. US; Baibulova M. S. et al: Syntheses from pyridylguanamines_ XP002764691. retrieved from STN Database accession No. 1990:406282 "abstract* & Bai Bulova, M. S. et al: Syntheses from pyridylguanamines", Izvestiya Akademii Nauk Kazakhskoi SSR, Seriya Khimicheskaya, (5), 40-2 Coden: IKAKAK; ISSN: 0002-3205, 1989.

Database CA [Online] Chemical Abstracts Service. Columbus.Ohio. US; Krimmer. Hans Peter et al: "Reaction of .beta.-mercapto .alpha.-amino acids with nitriles" .XP002764690.retrieved from STN Database accession No. 1988:529623* abstract* & Krimmer. Hans Peter et al: "Reaction of beta.-mercapto .alpha.-amino acids with nitriles".Chemiker-Zeitung â€¢ 111(12). 357-61 Coden: CMKZAT; ISSN: 0009-2894.1987.

(56) References Cited

OTHER PUBLICATIONS

Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, p. 13717-13725.
Dermer et al., "Another Anniversary for the War on Cancer", Bio/Technology, 1994, 12:320.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Drew, MGB, et al. "Solvent extraction and lanthanide complexation studies with new terdentate ligands containing two 1, 3, 5-triazine moieties." Dalton Transactions 2 (2004): 244-251.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Enholm, EJ., Jed M. Hastings, and Chris Edwards. "Hydrogen-Bonded Arrays Coupled by Cross-Metathesis." Synlett Feb. 2008 (2008): 203-206.
Freshney et al.,Culture of Animal Cells, A Manual of Basic Technique, Alan R. Liss, Inc., 1983, New York, p. 4.
Genetics Home Reference. "L2HGDH." accessed at <http://ghr.nlm.nih.gov/gene/L2HGDH> on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Gura. "Systems for identifying new drugs are often faulty," Science, 1997, 278(5340):1041-2.
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Holmes et al, 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
Im et al. "DNMT3A and IDH mutations in acute myeloid leukemia and other myeloid malignancies: Associations with prognosis and potential treatment strategies," Leukemia, 2014, 28:1774-1783.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.
Jennings et al, Expression and mutagenesis of mammalian cytosolic NADP+-specific isocitrate dehydrogenase, Biochemistry (1997)vol. 36, p. 13743-13747.
Johannessen et al. "Rapid conversion of mutant IDH1 from driver to passenger in model of human gliomagenesis," Molecular Cancer Resarch, 2016, 14(10): 976-83.
Johnson et al. "Relationships between drug activity in NCI preclinical in vitro and in vivo models and early clinical trials," British Journal of Cancer, 2001, 84(10): 1424-1431.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al "Ser95, Asn97, and Thr78 are important for the catalytic function of porcine NADP-dependent isocitrate dehydrogenase" Protein Science (2005) 14: pp. 140-147.
Kim et al. "Identification and Functional Characterization of a Novel, Tissue-specific NAD1-dependent Isocitrate Dehydrogenase b Subunit Isoform" JBC. Dec. 24, 1999, vol. 274 No 52 pp. 36866-36875.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al. "Pharmaceutical solid dispersion technology: A strategy to improve dissolution of poorly water-soluable drugs," Recent Patents on Drug Delivery and Formulation, 2013, 7:111-121.
"Study of orally adminisered AG-120 in subjects with advanced hematologic malignancies with an IDH1 mutation," clinicaltrials.gov retreived Feb. 6, 2017.
Birendra et al. "Evidence for clinical differentiation and differentiation syndrome in patients with acute myeloid leukemia and IDH1 mutations treated with the targeted mutant IDH1 inhibitor, AG-120," Clinical Lymphoma, Myeloma & Leukemia, 2016, 16(8):460-5.
Caunt et al. "MEK1 and MEK2 inhibitors and cancer therapy: the long and winding road," Nature Reviews Cancer, 2015, 15(10):577-592.
Dinardo et al. "Characteristics, clinical outcome, and prognostic significance of IDH mutations in AML," American Journal of Hematology, 2015, 90(8)732-736.
Dinardo et al. "Molecular profiling and relationship with clinical response in patients with IDH1 mutation-positive hematologic malignancies receiving AG-120, a first-in-class potent inhibitor of mutant IDH1, in addition to data from the completed dose escalation portion of the phase 1 study," Blood, 2015, 126:1306.
Green et al. "The prognostic significance of IDH1 mutations in younger adult patients with acute myeloid leukemia is dependent on FLT3/ITD status," Blood, 2010, 116(15):2779-2782.
Hansen et al. "AG-120, an oral, selective, first-in-class, potent inhibitor of mutant IDH1, reduces intracellular 2HG and induces cellular differentiation in TF-1 R132H cells and primary human IDH1 mutant AML patent samples treated ex vivo," Blood, 124(21):3734.
Hemerly et al. "Identification of several novel non-p.R132 IDH1 variants in thyroid carcinomas," European Journal of Endocrinology, 2010, 163(5):747-755.
Wei Chao et al. Teaching Materials of the 12th Five-Year Pain for the Relevant Majors of Pharmacy in the Specialty and Polytechnic Colleges, Pharmacy (2nd edition), Henan Science and Technology Press, 2012.
Yuan et al. "Role of IDH1 gene mutation in the genesis of glioblastoma," Medical Journal of Wuhan University, 2011, 32(2):164-166.
Dohner et al. "Acute myeloid leukemia," New England Journal of Medicine, 2015, 373:1136-52.
Ramos et al. "Current approaches in the treatment of relapsed and refractory acute myeloid leukemia," Journal of Clinical Medicine, 2015, 4(4):665-695.
International Search Report for PCT/US2016/057036 dated Jan. 12, 2017.
Kumar et al., "4-Anilinoquinoline triazines: A novel class of hybrid antimalarial agents" European Journal of Medicinal Chemistry (2011) vol. 46, pp. 676-690.

(56) References Cited

OTHER PUBLICATIONS

Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou. "IDH1: function follows form." SciBX, 2009, 1-2.
Lowe, "Good old medicinal chemistry: what can you get away with?," Blog "In the Pipeline," entry of Nov. 2, 2010.
Lutker et al, "Crystal Polymorphism in a Carbamazepine Derivative: Oxcarbazepine". NIH Public Access. J Pharm Sci. Feb. 2010; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Maison, "Multicomponent synthesis of novel amino acid-nucleobase chimeras: a versatile approach to PNA-monomers," Bioorganic & Medicinal Chemistry (2000) vol. 8, pp. 1343-1360.
May et al, How many species are there on earth, Science (1988) vol. 241, p. 1441.
Mcrobbie et al. "MRI from Picture to Proton," Cambridge University Press, 2007, pp. 307-308.
Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.
Mikhaylichenko, Svetlana, et al. "Synthesis and structure of new 1,2, 3-triazolyl substituted 1,3, 5-triazines." European Journal of Chemistry 3.1 (2012): 1-9.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science vol. 321 (2008) pp. 1807-1812 and Supplemental Data.
Pitts et al., "Rapid Synthesis of Triazine Inhibitors of Inosine Monophosphate Dehydrogenase," Bioorganic & Medicinal Chemistry Letters (2002) vol. 12, pp. 2137-2140.
Pollard et al, "Cancer. Puzzling patterns of predisposition." Science. Apr. 10, 2009, vol. 324, 1-5,15-16, 18-22,35-38 No. 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Jul. 3, 2008, CAS Registration No. 1032461-94-1.
Registry (STN) [online], Jul. 3, 2008, CAS Registration No. 1032470-22-6.
Registry (STN) [online], Jul. 4, 2008, CAS Registration No. 1032747-65-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Apr. 16, 2010, CAS Registration No. 1219379-97-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Rohle et al. "An Inhibitor of Mutant IDH1 Delays Growth and Promotes Differentiation of Glioma Cells" Science, vol. 340, No. 6132 pp. 626-630 (2013).
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Search Report for SG 11201600185U dated Nov. 16, 2016.
Serajuddin et al. "Solid dispersion of poorly water-soluable drugs: early promises, subsequent problems, and recent breakthroughs," Journal of Pharmaceutical Sciences, 1999, 88(10):1058-1066.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
Shih et al. "The Role of Mutations in Epigenetic Regulators in Myeloid Malignancies" Nature Reviews Cancer (2012) vol. 12, No. 9, pp. 599-612.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385 English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-

(56) References Cited

OTHER PUBLICATIONS 3,3-dimethyl-8-phenyl-", disclosed in Paronikyan et al. Armyanskii Khimicheskii Zhumal, 1990, vol. 43, No. 8.

Astellas, "Dose escalation study investigating the safety, tolerability, pharmacokinetics, pharmacodynamics of ASP2215 in patients with relapsed or refractory acute myeloid leukemia," (Astellas Pharma Global Development, Inc., https://clinicaltrials.gov/ct2/history/NCT02014558?V_11=View#StudyPageTop, Dec. 12, 2013 (v1), obtained from the internet Jun. 21, 2019).

Brittain et al. "Polymorphism in pharmaceutical solids," 2009, chapter 1, p. 1-10 and chapter 5, 183-226.

Byrn et al. "Pharmaceutical solids: A strategic approach to regulatory considerations," Pharmaceutical Research, 1995, 12(7):945-954.

Caira et al. "Crystalline polymorphism of organic compounds," Topics in Current Chemistry, Springer, Berlin, DE, 1998, vol. 198, pp. 163-208.

Dohner et al. "Impact of genetic features on treatment decisions in AML," ASH Education Program Book, 2011, 1:36-42.

Emadi et al. "Presence of isocitrate dehydrogenase mutations may predict clinical response to hypomethylating agents in patients with acute myeloid leukemia," American Journal of Hematology, 2015, 90(5):E77-E79.

Friesen et al. "Hydroxypropyl Methylcellulose Acetate Succinate-Based Spray-Dried Dispersions: An Overview," Molecular Pharmaceutics, 2008, 5(6):1003-1019.

Hashida, Design and Evaluation of Oral Administration Formulations, Jiho Inc., 1995, 172-185.

Hashida, Design and Evaluation of Oral Administration Formulations, Jiho Inc., 1995, 76-79.

Huang et al. "Fundamental aspects of solid dispersion technology for poorly soluble drugs," Acta Pharmaceutica Sinica B, 2014, 4(1):18-25.

Lazzarino et al. "Mitoxantrone and etoposide: An effective regimen for refractory or relapsed acute myelogenous eukemia," European Journal of Haematology, 1989, 43:411-416.

Levis et al. "Results of a first-in-human, phase I/II trial of ASP2215, a selective, potent inhibitor of FLT3/Axl in patients with relapsed or refractory (R/R) acute myeloid leukemia," Journal of Clinical Oncology, 2015, 33(15 suppl):7003.

Shafer et al. "Update on rational tareted therapy in AML," Blood Reviews, 2016, 30:275-283.

Shuichi et al. "Long-term follow-up of the randomized JALSG AML 201 study comparing high dose Ara-C therapy with conventional consolidation therapy in adult acute myeloid leukemia (AML)," Blood, 2008, 112(11):135.

Goodman and Gilman's "The Pharmacological Basis of Therapeutics" 10th Ed., p. 54-56 (2001).

Stein et al, "Ivosidenib or Enasidenib Combined with Intensive Chemotherapy in Patients with Newly Diagnosed AML: A Phase 1 Study" Downloaded from http://ashpublications.org/blood/article-pdfdoi/10.1182/blood.202007233/1760576/blood.2020007233.pdfby Copyright Clearance Center user on Oct. 15, 2020.

Morris et al, "Epidemiology of Cancer" (2005).

* cited by examiner

COMBINATION THERAPY FOR TREATING MALIGNANCIES

CLAIM OF PRIORITY

This application is a national stage application under 35 U.S.C. 371 of International Application No. PCT/US2016/057036 filed Oct. 14, 2016, which claims priority from U.S. Ser. No. 62/242,267 filed Oct. 15, 2015, and U.S. Ser. No. 62/255,253 filed Nov. 13, 2015, each of which is incorporated herein by reference in its entirety.

FIELD

Provided herein are combination therapies for treating acute myeloid leukemia. In one embodiment, the therapies involve treatment with an IDH1 inhibitor and an induction and a consolidation therapy.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December-2008) to UniProtKB; Kullmann et al., Submitted (June-1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate thereby reducing NAD (NADP$^+$) to NADH (NADPH), e.g., in the forward reaction:

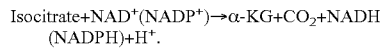
Isocitrate+NAD$^+$(NADP$^+$)→α-KG+CO$_2$+NADH (NADPH)+H$^+$.

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al, Nature 2009, 462:739-44).

The development of selective inhibitors of IDH1 mutant enzyme has provided the possibility of therapeutic benefit to AML patients carrying the IDH1 mutation. There have been successful responses in the clinic with decreased blast population and benefit of differentiated functional blood cells. However, the genetic load is present in the patients even with good overall response. Therefore, there is a need for improved therapies for treating acute myeloid leukemia having IDH1 mutations.

SUMMARY

In one embodiment, provided herein are methods of treating acute myeloid leukemia (AML) characterized by the presence of a mutant allele of IDH1, by administering to a subject a therapeutically effective amount of a combination of a mutant IDH1 inhibitor and an induction and a consolidation therapy. In one embodiment, the AML, characterized by the presence of a mutant allele of IDH1, is refractory, or relapsed AML.

In one embodiment, the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, or a pharmaceutically acceptable salt, solvate, tautomer, stereoisomer, isotopologue, prodrug or a polymorph thereof (COMPOUND 2).

In one embodiment, the method comprises administering to a subject a therapeutically effective amount of COMPOUND 2, and an induction and a consolidation therapy.

In certain embodiments, the induction therapy for treatment of AML comprises administering cytarabine with either daunorubicin or idarubicin. In certain embodiments, the induction therapy comprises administering cytarabine with daunorubicin. In certain embodiments, the induction therapy comprises administering cytarabine with idarubicin.

In certain embodiments, the consolidation therapy for treatment of AML comprises administering i) mitoxantrone with etoposide or ii) cytarabine. In certain embodiments, the consolidation therapy comprises administering mitoxantrone with etoposide. In certain embodiments, consolidation therapy comprises administering cytarabine.

In one embodiment, provided herein are methods of treating AML characterized by the presence of a mutant allele of IDH, by administering to a subject a combination of a therapeutically effective amount of a mutant IDH1 inhibitor and an induction and a consolidation therapy, wherein a) the induction therapy comprises administering cytarabine with either daunorubicin or idarubicin, and b) the consolidation therapy comprises administering i) mitoxantrone with etoposide or ii) cytarabine. In one embodiment, the mutant IDH1 inhibitor is COMPOUND 2.

In one embodiment, provided herein are methods of treating AML characterized by the presence of a mutant allele of IDH1, by administering to a subject a combination of a therapeutically effective amount of a mutant IDH1 inhibitor and an induction and a consolidation therapy, wherein a) the induction therapy comprises administering cytarabine with daunorubicin, and b) the consolidation therapy comprises administering mitoxantrone with etoposide. In one embodiment, the mutant IDH1 inhibitor is COMPOUND 2.

In one embodiment, provided herein are methods of treating AML characterized by the presence of a mutant allele of IDH1, by administering to a subject a combination of a therapeutically effective amount of a mutant IDH1 inhibitor and an induction and a consolidation therapy, wherein a) the induction therapy comprises administering cytarabine with daunorubicin, and b) the consolidation therapy comprises administering cytarabine. In one embodiment, the mutant IDH1 inhibitor is COMPOUND 2.

In one embodiment, provided herein are methods of treating AML characterized by the presence of a mutant allele of IDH1, by administering to a subject a combination of a therapeutically effective amount of a mutant IDH1 inhibitor and an induction and a consolidation therapy, wherein a) the induction therapy comprises administering cytarabine with idarubicin, and b) the consolidation therapy comprises administering mitoxantrone with etoposide. In one embodiment, the mutant IDH1 inhibitor is COMPOUND 2.

In one embodiment, provided herein are methods of treating AML characterized by the presence of a mutant allele of IDH1, by administering to a subject a combination of a therapeutically effective amount of a mutant IDH1 inhibitor and an induction and a consolidation therapy, wherein a) the induction therapy comprises administering cytarabine with idarubicin, and b) the consolidation therapy comprises administering cytarabine. In one embodiment, the mutant IDH1 inhibitor is COMPOUND 2.

In one embodiment, provided herein are methods of treating AML characterized by the presence of a mutant allele of IDH1, by administering to a subject a combination of a pharmaceutical composition comprising a therapeutically effective amount of COMPOUND 2 and an induction and a consolidation therapy for AML.

In one embodiment, provided herein is a method of treating AML, wherein AML is selected from newly diagnosed AML, untreated AML, AML arising from myelodysplastic syndrome (MDS), AML arising from antecedent hematologic disorder (AHD) and AML arising after exposure to genotoxic injury. In certain embodiments, the genotoxic injury results from radiation and/or chemotherapy. In one embodiment, provided herein is a method of treating AML arising after exposure to genotoxic injury resulting from radiation and/or chemotherapy.

DETAILED DESCRIPTION

Figure 1:
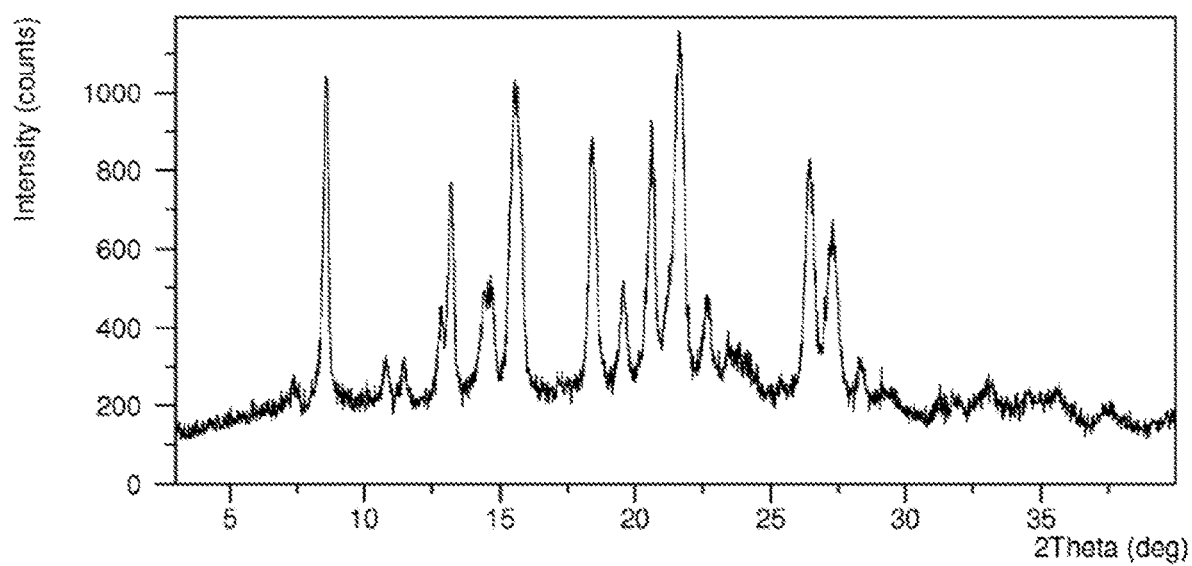
FIG. 1 is an X-ray powder diffractogram (XPRD) of COMPOUND 2 form 1.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH1 inhibitor" or "inhibitor of IDH1 mutant(s)" means a molecule e.g., a polypeptide, peptide, or small molecule (e.g., a molecule of less than 1,000 daltons), or aptomer, that binds to an IDH1 mutant subunit and inhibits neoactivity, e.g., by inhibiting formation of a dimer, e.g., a homodimer of mutant IDH1 subunits or a heterodimer of a mutant and a wildtype subunit. In some embodiments, the neoactivity inhibition is at least about 60%, 70%, 80%, 90%, 95% or 99% as compared to the activity in the absence of the mutant IDH1 inhibitor. In one embodiment, the mutant IDH1 inhibitor is COMPOUND 2.

The term "elevated levels of 2HG" means 10%, 20% 30%, 50%, 75%, 100%, 200%, 500% or more 2HG is present in a subject that carries a mutant IDH1 allele than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an advanced hematologic malignancy, such as acute myelogenous leukemia (AML), myelodysplastic syndrome (MDS, myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1), lessen the severity of the disease/disorder or improve the symptoms associated with the disease/disorder.

An amount of a compound, including a pharmaceutically acceptable salt, solvate, tautomer, stereoisomer, isotopologue, prodrug or a polymorph thereof, effective to treat a disorder, or a "therapeutically effective amount" or "therapeutically effective dose" refers to an amount of the compound, or a pharmaceutically acceptable salt thereof, including a pharmaceutically acceptable salt, solvate, tautomer, stereoisomer, isotopologue, prodrug or a polymorph thereof, which is effective, upon single or multiple dose administration to a subject, in treating a cell, or in curing, alleviating, relieving or improving a subject with a disorder beyond that expected in the absence of such treatment.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 2 may be produced as one or more single crystalline forms of COMPOUND 2. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 2 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a COMPOUND 2 that is at least 70% crystalline. In other embodiments, substantially crystalline refers to a COMPOUND 2 that is at least 90% crystalline.

The term "isolated" refers to forms that may be at least a particular weight percent of a particular crystalline form of compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.* Vol. 66, pp. 1-19.

The term "acute myeloid leukemia (AML)", as used herein, refers to cancer of the myeloid line of blood cells, characterized by the rapid growth of abnormal white blood cells that accumulate in the bone marrow and interfere with the production of normal blood cells. In one embodiment, the AML is selected from newly diagnosed AML, untreated AML, AML arising from myelodysplastic syndrome (MDS), AML arising from antecedent hematologic disorder (AHD) and AML arising after exposure to genotoxic injury.

The term "refractory AML" as used herein, refers to an AML in which the high level of white blood cells does not decrease in response to a treatment.

The term "relapsed AML" as used herein, refers to an AML which does not respond to a treatment.

The term "AML induction therapy", as used herein, refers to a therapy given with the goal of rapidly restoring normal bone marrow function, i.e., to induce remission.

The term "AML consolidation therapy", as used herein, refers to a therapy given to maintain remission achieved as a result of the induction therapy.

The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compounds

COMPOUND 2 is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, a pharmaceutically acceptable salt, solvate, tautomer, stereoisomer, isotopologue, prodrug, or a polymorph thereof. COMPOUND 2 has the following chemical structure:

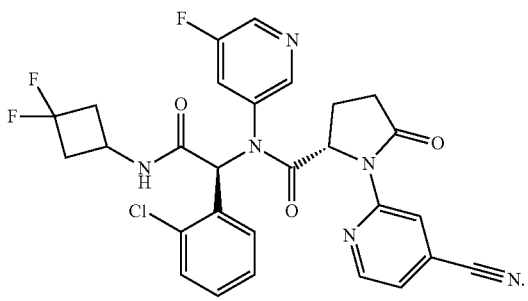 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

COMPOUND 2 may also comprise one or more isotopic substitutions. For example, H may be in any isotopic form ("Isotopologues"), including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like. For example, COMPOUND 2 is enriched in a specific isotopic form of H, C and/or O by at least about 60%, 65%, 70%, 75%, 80%, 85%, 90%, 95%, 96%, 97%, 98%, or 99%.

COMPOUND 2 in certain embodiments may also be represented in multiple tautomeric forms, in such instances, one aspect of the invention expressly includes all tautomeric forms of COMPOUND 2 described herein, even though only a single tautomeric form may be represented (e.g., keto-enol tautomers). All such isomeric forms of COMPOUND 2 are expressly included herein. Synthesis of COMPOUND 2 is described in US published application US-2013-0190249-A1 published Jul. 25, 2013, which is incorporated by reference in its entirety.

It may be convenient or desirable to prepare, purify, and/or handle a corresponding salt of COMPOUND 2, for example, a pharmaceutically-acceptable salt. Examples of pharmaceutically acceptable salts are discussed in Berge et al., 1977, "Pharmaceutically Acceptable Salts." *J. Pharm. Sci.* Vol. 66, pp. 1-19.

For example, if COMPOUND 2 is anionic, or has a functional group which may be anionic (e.g., —NH— may be —N—$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4$$^+$.

If COMPOUND 2 is cationic, or has a functional group that may be cationic (e.g., —NHR may be —NH$_2$R$^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

COMPOUND 2 for use in the methods and pharmaceutical compositions provided herein therefore includes COMPOUND 2 itself, as well as its pharmaceutically acceptable salts, solvates, tautomers, stereoisomers, isotopologues, prodrugs or polymorphs. COMPOUND 2 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 2 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 2. In certain embodiments, the present disclosure provides compositions comprising COMPOUND 2 in a form described herein. In some embodiments of provided compositions, COMPOUND 2 is present as a mixture of one or more solid forms; in some embodiments of provided compositions, COMPOUND 2 is present in a single form.

In one embodiment, COMPOUND 2 is a single crystalline form, or any one of the single crystalline forms described herein. Synthesis of crystalline forms of COMPOUND 2 is described in international application publications WO 2015/138837 and WO 2015/138839, both published Sep. 17, 2015, both incorporated by reference herein in their entireties. Also provided are pharmaceutical compositions comprising at least one pharmaceutically acceptable carrier or diluent; and COMPOUND 2, wherein COMPOUND 2 is a single crystalline form, or any one of the crystalline forms being described herein. Also provided are uses of COMPOUND 2, wherein COMPOUND 2 is a single crystalline form, or any one of the single crystalline forms described herein, to prepare a pharmaceutical composition.

Provided herein is an assortment of characterizing information to describe the crystalline forms of COMPOUND 2. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 2 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 2 is crystalline, the remainder of COMPOUND 2 is the amorphous form of COMPOUND 2. Non-limiting examples of crystalline COMPOUND 2 include a single crystalline form of compound 1 or a mixture of different single crystalline forms. In some embodiments, COMPOUND 2 is at least 90% by weight crystalline. In some other embodiments, COMPOUND 2 is at least 95% by weight crystalline.

In another embodiment, a particular percentage by weight of the crystalline COMPOUND 2 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, COMPOUND 2 is at least 90% by weight of a single crystalline form. In another embodiment, COMPOUND 2 is at least 95% by weight of a single crystalline form.

In the following description of COMPOUND 2, embodiments of the invention may be described with reference to a particular crystalline form of COMPOUND 2, as characterized by one or more properties as discussed herein. The descriptions characterizing the crystalline forms may also be used to describe the mixture of different crystalline forms that may be present in a crystalline COMPOUND 2. However, the particular crystalline forms of COMPOUND 2 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 2 may vary by ±0.2° depending upon the instrument used to obtain the data. The intensity of the XRPD peaks described in Tables 1 to 2 may vary by 10%.

Form 1

In one embodiment, a single crystalline form, Form 1, of COMPOUND 2 is characterized by the X-ray powder diffraction (XRPD) pattern shown in FIG. 1, and data shown in Table 1, obtained using CuKa radiation. In a particular embodiment, the polymorph can be characterized by one or more of the peaks taken from FIG. 1, as shown in Table 1. For example, the polymorph can be characterized by one or two or three or four or five or six or seven or eight or nine of the peaks shown in Table 1.

TABLE 1

| Angle 2-Theta° | Intensity % |
| --- | --- |
| 8.6 | 90.3 |
| 13.2 | 60.0 |
| 15.6 | 85.5 |
| 18.5 | 72.5 |
| 19.6 | 31.5 |
| 20.6 | 71.6 |
| 21.6 | 100.0 |
| 26.4 | 64.2 |
| 27.3 | 45.6 |

In another embodiment, Form 1 can be characterized by the peaks identified at 2θ angles of 8.6, 15.6, 18.5, 20.6, 21.6, and 26.4°. In another embodiment, Form 1 can be characterized by the peaks identified at 2θ angles of 8.6, 15.6, 18.5, and 21.6°.

Figure 2:
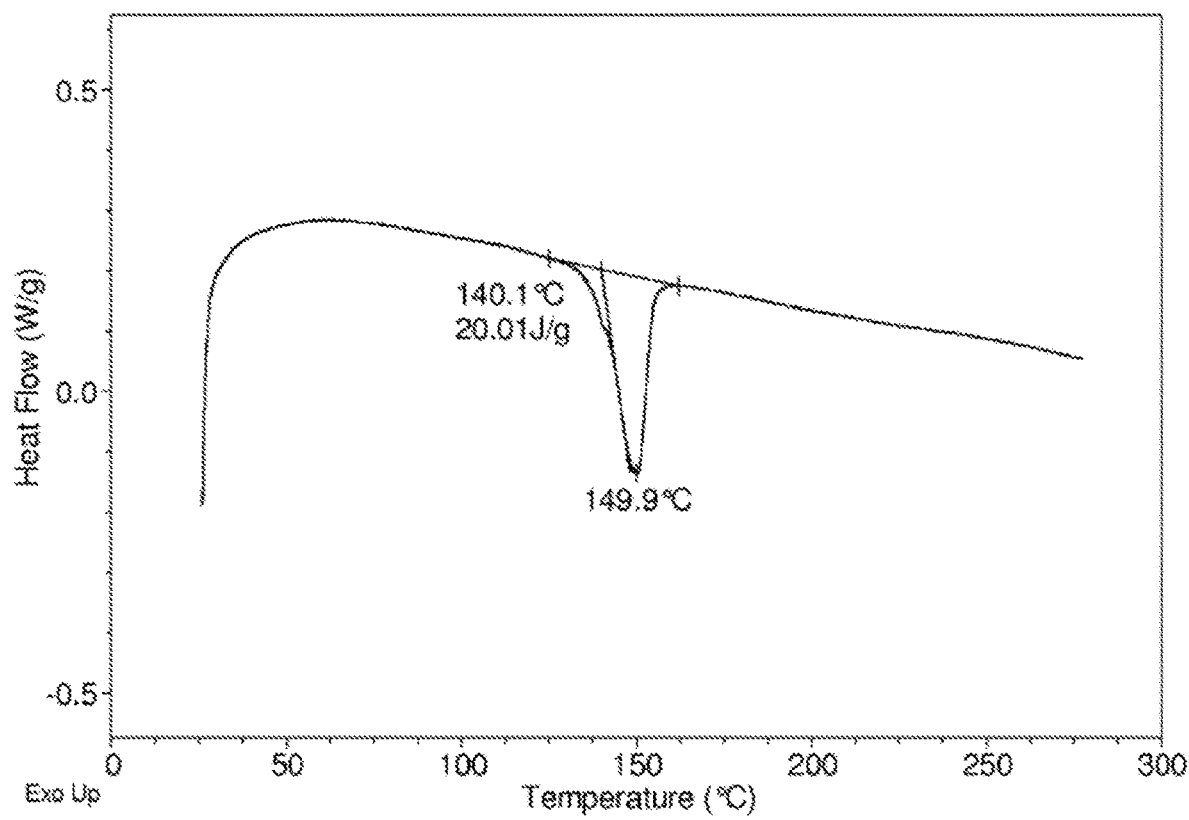
FIG. 2 is a differential scanning calorimetry (DSC) profile of COMPOUND 2 form 1.

In another embodiment, Form 1 can be characterized by the differential scanning calorimetry profile (DSC) shown in FIG. 2. The DSC graph plots the heat flow as a function of temperature from a sample, the temperature rate change being about 10° C./min. The profile is characterized by an endothermic transition with an onset temperature of about 140.1° C. with a melt at about 149.9° C.

Figure 3:
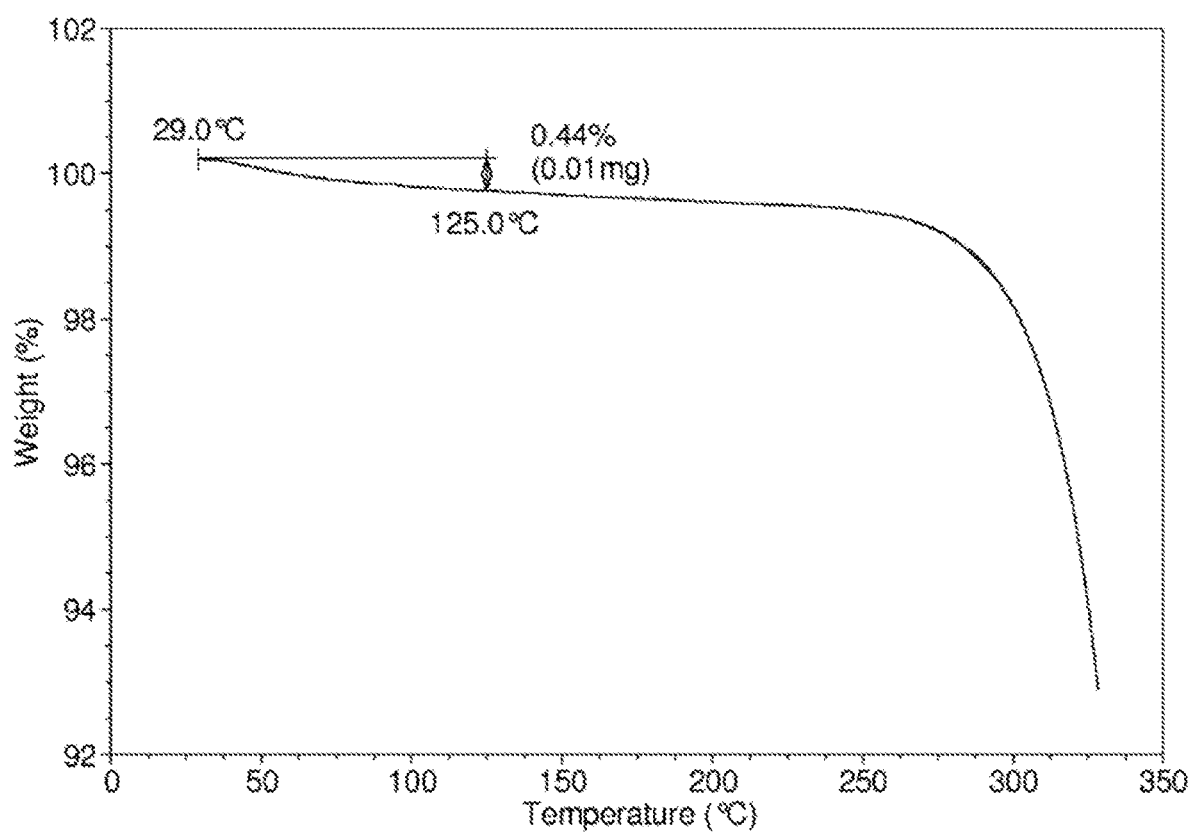
FIG. 3 is a thermal gravimetric analysis (TGA) profile of COMPOUND 2 form 1.

In another embodiment, Form 1 can be characterized by thermal gravimetric analysis (TGA) shown in FIG. 3. The TGA profile graphs the percent loss of weight of the sample as a function of temperature, the temperature rate change being about 10° C./min. The weight loss represents a loss of about 0.44% of the weight of the sample as the temperature is changed from about 29.0° C. to 125.0° C.

Form 2

Figure 4:
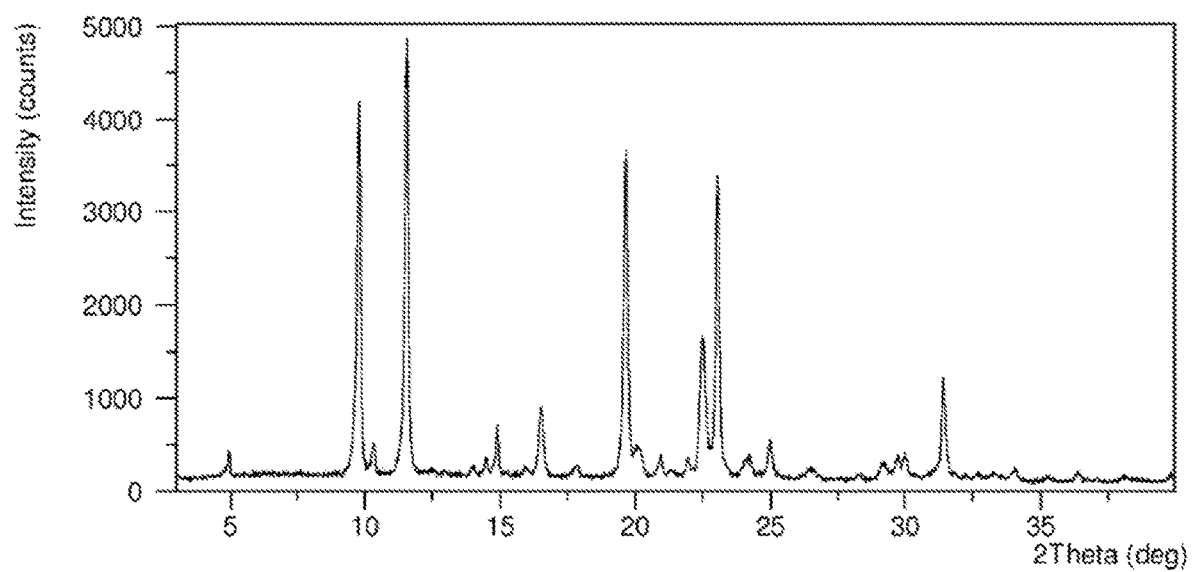
FIG. 4 is an X-ray powder diffractogram (XPRD) of COMPOUND 2 form 2.

In one embodiment, a single crystalline form, Form 2, of the COMPOUND 2 is characterized by the X-ray powder diffraction (XRPD) pattern shown in FIG. 4, and data shown in Table 2, obtained using CuKa radiation. In a particular embodiment, the polymorph can be characterized by one or more of the peaks taken from FIG. 4, as shown in Table 2. For example, the polymorph can be characterized by one or two or three or four or five or six or seven or eight or nine or ten of the peaks shown in Table 2.

TABLE 2

| Angle 2-Theta° | Intensity % |
| --- | --- |
| 9.8 | 85.6 |
| 11.6 | 100.0 |
| 14.9 | 11.4 |
| 16.5 | 15.3 |
| 19.6 | 75.2 |
| 20.1 | 7.3 |
| 22.5 | 32.6 |
| 23.0 | 69.4 |
| 25.0 | 8.9 |
| 31.4 | 22.0 |

In another embodiment, Form 2 can be characterized by the peaks identified at 2θ angles of 9.8, 11.6, 19.6, 22.5, 23.0, and 31.4°. In another embodiment, Form 2 can be characterized by the peaks identified at 2θ angles of 9.8, 11.6, 19.6, and 23.0°.

Figure 5:
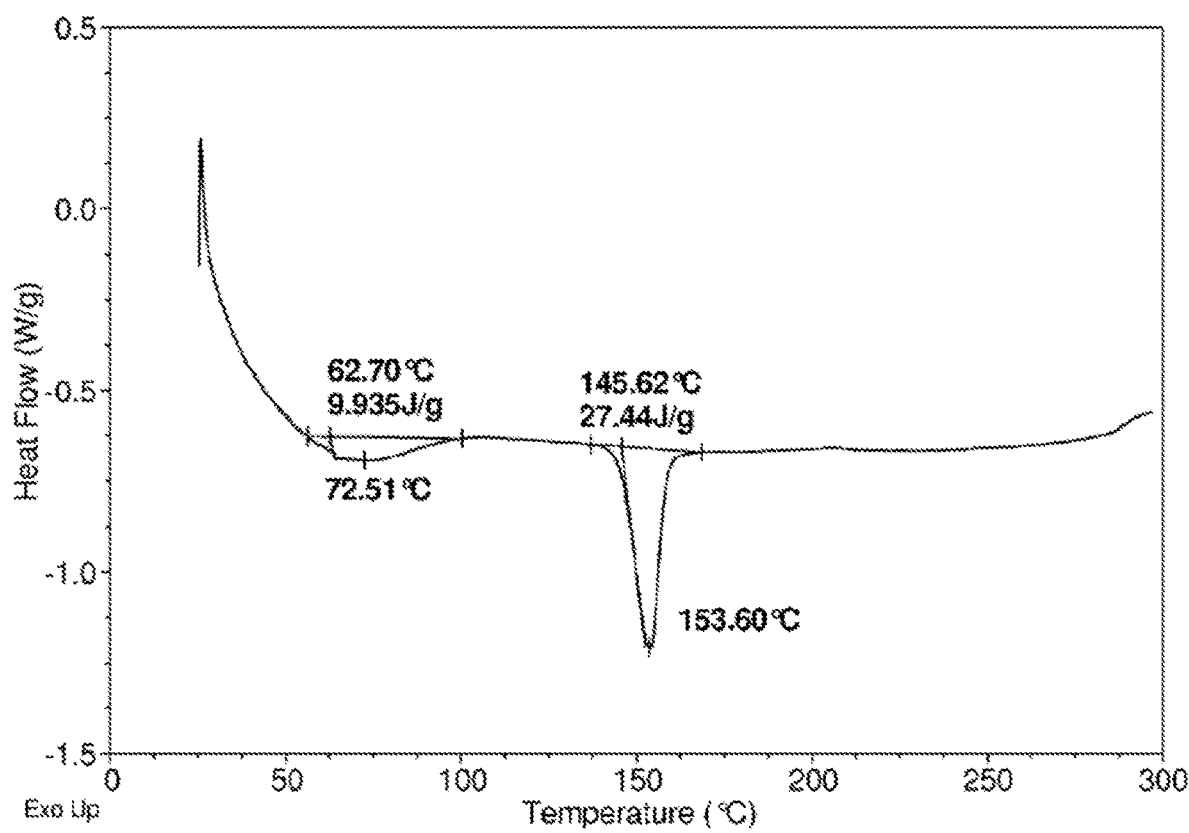
FIG. 5 is a differential scanning calorimetry (DSC) profile of COMPOUND 2 form 2.

In another embodiment, Form 2 can be characterized by the differential scanning calorimetry profile (DSC) shown in FIG. 5. The DSC graph plots the heat flow as a function of temperature from a sample, the temperature rate change being about 10° C./min. The profile is characterized by an endothermic transition with an onset temperature of about 62.7° C. with a melt at about 72.5° C., and an endothermic transition with an onset temperature of about 145.6° C. with a melt at about 153.6° C.

Figure 6:
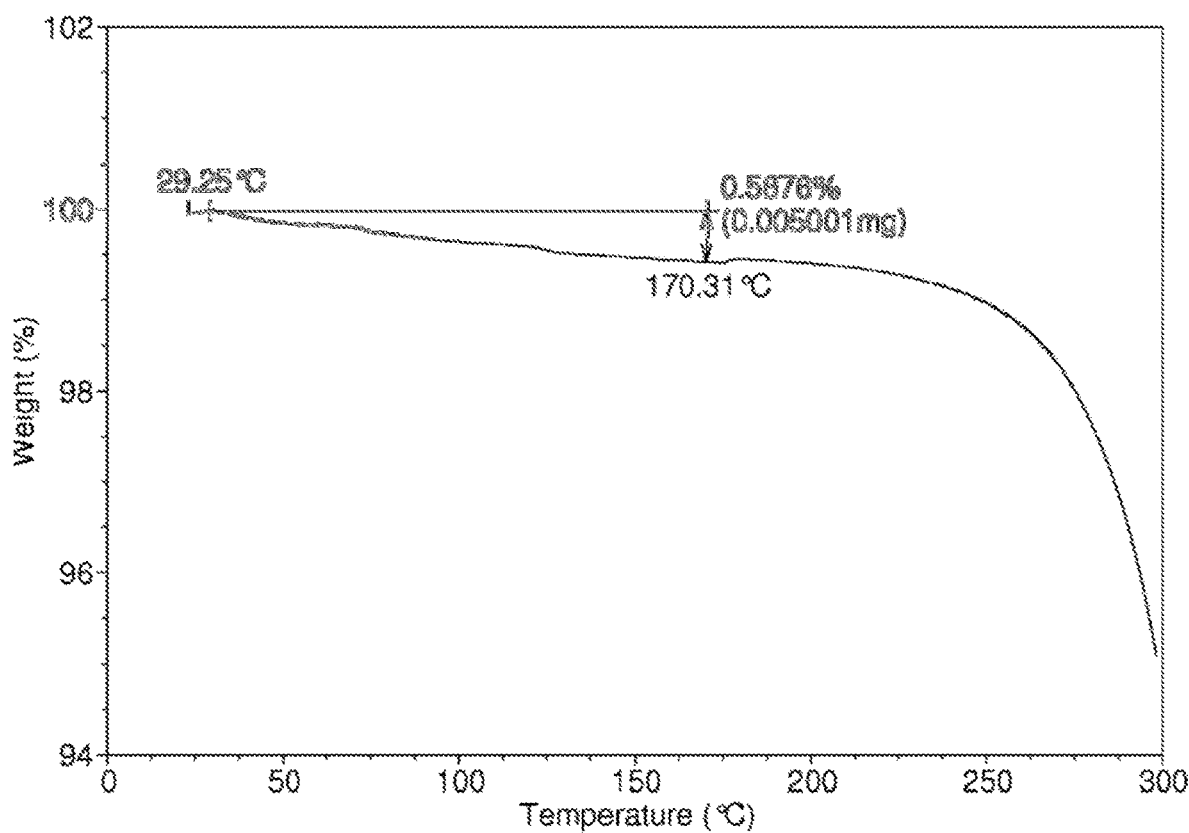
FIG. 6 is a thermal gravimetric analysis (TGA) profile of COMPOUND 2 form 2.

In another embodiment, Form 2 can be characterized by thermal gravimetric analysis (TGA) shown in FIG. 6. The TGA profile graphs the percent loss of weight of the sample as a function of temperature, the temperature rate change being about 10° C./min. The weight loss represents a loss of about 0.57% of the weight of the sample as the temperature is changed from about 29.3° C. to 170.3° C.

Other embodiments are directed to a single crystalline form of COMPOUND 2 characterized by a combination of the aforementioned characteristics of any of the single crystalline forms discussed herein. The characterization may be by any combination of one or more of the XRPD, TGA, and DSC described for a particular polymorph. For example, the single crystalline form of COMPOUND 2 may be characterized by any combination of the XRPD results regarding the position of the major peaks in a XRPD scan; and/or any combination of one or more of parameters derived from data obtained from a XRPD scan. The single crystalline form of COMPOUND 2 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of COMPOUND 2 as determined by water sorption/desorption measurements over a range of relative humidity (e.g., 0% to 90%) may also characterize a single crystalline form of COMPOUND 2.

Compositions and Routes of Administration

In one embodiment, the pharmaceutical composition comprises COMPOUND 2 and an excipient. In one embodiment, the pharmaceutical composition that comprises COMPOUND 2 and an excipient, is for oral administration. In one embodiment, the excipient is a diluent, a binder, a disintegrant, a wetting agent, a stabilizer, a glidant, and/or a lubricant.

In one embodiment, the pharmaceutical composition comprises cytarabine and a diluent or solvent. In one embodiment, the pharmaceutical composition that comprises cytarabine and a diluent or solvent, is for intravenous injection.

In one embodiment, the pharmaceutical composition comprises daunorubicin and a diluent or solvent. In one embodiment, the pharmaceutical composition that comprises daunorubicin and a diluent or solvent, is for intravenous injection.

In one embodiment, the pharmaceutical composition comprises idarubicin and a diluent or solvent. In one embodiment, the pharmaceutical composition that comprises idarubicin and a diluent or solvent, is for intravenous injection.

In one embodiment, the pharmaceutical composition comprises mitoxantrone and a diluent or solvent. In one embodiment, the pharmaceutical composition that comprises mitoxantrone and a diluent or solvent, is for intravenous injection.

In one embodiment, the pharmaceutical composition comprises etoposide and a diluent or solvent. In one embodiment, the pharmaceutical composition that comprises etoposide and a diluent or solvent, is for intravenous injection.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of COMPOUND 2 described herein.

In one embodiment, the pharmaceutical composition comprises COMPOUND 2 and an excipient. In one embodiment, the pharmaceutical composition that comprises COMPOUND 2 and an excipient, is for oral administration. In one embodiment, the excipient is a diluent, a binder, a disintegrant, a wetting agent, a stabilizer, a glidant, or a lubricant.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of Pharmaceutically acceptable solid, liquid, or other dosage forms may also be used for the purposes of formulation.

Particular embodiments herein provide solid oral dosage forms that are tablets or capsules. In certain embodiments, the formulation is a tablet comprising COMPOUND 2. In certain embodiments, the formulation is a tablet comprising COMPOUND 2. In certain embodiments, the formulation is a capsule comprising COMPOUND 2. In certain embodiments, the formulation is a capsule comprising COMPOUND 2. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of COMPOUND 2 for the preparation of a pharmaceutical composition for treating a malignancy, characterized by the presence of a mutant allele of IDH1, wherein the composition is prepared for oral administration. In certain embodiments, embodiments herein encompass the use of COMPOUND 2 for the preparation of a pharmaceutical composition for treating a malignancy, characterized by the presence of a mutant allele of IDH1, wherein the composition is prepared for oral administration.

In certain embodiments, embodiments herein encompass the use of cytarabine, daunorubicin, idarubicin, mitoxantrone, and/or etoposide for the preparation of a pharmaceutical composition for treating a malignancy, characterized by the presence of a mutant allele of IDH1, wherein the composition is prepared for intravenous administration.

The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Solid Dispersions of COMPOUND 2

In certain embodiment, COMPOUND 2 is administered in compositions, comprising COMPOUND 2, and one or more polymer(s) as part of a solid dispersion (e.g., an amorphous solid dispersion). In some embodiments, the solid dispersion comprises COMPOUND 2, and one or more polymer(s). In some embodiments, the solid dispersion comprises COMPOUND 2, one or more polymer(s), and one or more surfactant(s). In some embodiments, the solid dispersion comprises COMPOUND 2, and one polymer. In some embodiments, the solid dispersion comprises COMPOUND 2, one polymer, and a surfactant.

In certain embodiment, the solid dispersions provided herein, comprising COMPOUND 2, enhance the solubility of COMPOUND 2 relative to a neat crystalline form of COMPOUND 2 (e.g., Form 1 or Form 2), and thus provide improved exposure upon oral dosing of the solid dispersion to a subject. In one embodiment, the solid dispersion comprises COMPOUND 2, one or more polymer(s), and optionally one or more solubility enhancing surfactant.

For example, the aqueous solubility of Form 1 is about 0.025 mg/mL to about 0.035 mg/mL and the aqueous solubility of Form 2 is about 0.008 mg/mL to about 0.010 mg/mL.

Form 2 has a solubility of about 0.018 mg/mL in fasted state simulated intestinal fluid (FASSIF) at a pH of 6.1 at 4 hours. In comparison, amorphous spray-dried dispersions have a solubility of about 0.05 mg/mL to about 0.50 mg/mL in FASSIF at 3 hours.

In some embodiments, the solid dispersion exhibits at least about 20%, at least about 30%, at least about 40%, at least about 50%, at least about 60%, at least about 70%, at least about 80%, or at least about 90% higher exposure of COMPOUND 2, when administered to a subject as compared to administration of in-situ amorphous COMPOUND 2. In some embodiments, the solid dispersion exhibits at least about 20%, at least about 30%, at least about 40%, at least about 50%, at least about 60%, at least about 70%, at least about 80%, or at least about 90% higher exposure of COMPOUND 2, when administered to a subject as compared to administration of neat crystalline COMPOUND 2.

In rat and monkey pharmacokinetics studies, modest exposure improvement is observed upon administration of solid dispersion oral dosage forms as compared to in-situ amorphous dosing shows. For example, a solid dispersion containing 50% w/w COMPOUND 2 and 50% w/w Polyvinyl Acetate Phthalate (PVAP) has approximately two-fold higher exposure as compared to in-situ amorphous COMPOUND 2 in male Sprague Dawley rats. There is no significant difference in exposure between a solid dispersion containing 70% w/w COMPOUND 2 and 30% w/w oral dosage form as compared to in-situ amorphous COMPOUND 2. In male cynomolgus monkeys, the exposure of a solid dispersion containing 50% w/w COMPOUND 2 and 50% w/w hydroxypropylmethylcellulose acetate succinate, also known as hypromellose acetate succinate, (HPMCAS) shows no significant difference as compared to the in-situ amorphous COMPOUND 2. Similarly, a solid dispersion containing 50% w/w COMPOUND 2 and 50% w/w hydroxypropylmethylcellulose also known as hypromellose phthalate (HPMC-Phthalate) shows no significant difference as compared to the in-situ amorphous COMPOUND 2. While in-situ amorphous therapeutic compounds are commonly used for dosing in animal studies, they are not suitable dosage forms for dosing in humans.

As described in the rat pharmacokinetics study of Example 4, COMPOUND 2 exposure is improved when solid dispersion dosage forms are administered as compared to neat crystalline COMPOUND 2 Form 2.

In some embodiments, at least a portion of COMPOUND 2, in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline COMPOUND 2.

In some embodiments, the composition is an amorphous solid (e.g. spray dried) dispersion comprising COMPOUND 2, and a polymer. The amorphous solid dispersion can include, e.g., less than about 30%, less than about 20%, less than about 15%, less than about 10%, less than about 5%, less than about 4%, less than about 3%, less than about 2%, or less than about 1% of crystalline COMPOUND 2, e.g., be substantially free of crystalline COMPOUND 2.

In one embodiment, the solid dispersion exhibits a predetermined level of physical and/or chemical stability. E.g., the solid dispersion retains about 50%, about 60%, about 70%, about 80%, about 90%, about 95%, about 98%, or about 99%, of amorphous COMPOUND 2, when stored at 25° C. in a closed water tight container, e.g., an amber glass vial, high density polyethylene (HDPE) container or double polyethylene bags with twisted nylon tie placed in an HDPE container with desiccant.

In some embodiments, the polymer increases the chemical or physical stability (e.g., as measured by a Modulated Differential Scanning calorimeter) of COMPOUND 2, when stored (e.g., at 2-8° C., e.g. 4° C. or at room temperature) by at least about 10% (e.g., by at least about 20%, by at least about 30%, by at least about 40%, by at least about 50%, by at least about 60%, by at least about 70%, by at least about 80%, or by at least about 90%) compared to amorphous COMPOUND 2, without being in the presence of the polymer.

A solid dispersion generally exhibits a glass transition temperature, where the dispersion makes a transition from a glassy solid to a rubbery composition. In general, the higher the glass transition temperature, the greater the physical stability of the dispersion. The existence of a glass transition temperature generally indicates that at least a large portion of the composition (e.g., dispersion) is in an amorphous state. The glass transition temperature (Tg) of a solid dispersion suitable for pharmaceutical applications is generally at least about 50° C. In some embodiments, higher temperatures are preferred. Therefore, in some embodiments, a solid dispersion disclosed herein has a Tg of at least about 100° C. (e.g., at least about 100° C., at least about 105° C., at least about 110° C., at least about 115° C., at least about 120° C., at least about 125° C., at least about 130° C., at least about 135° C., at least about 140° C., at least about 150° C., at least about 160° C., at least about 170° C., at least about 175° C., at least about 180° C., or at least about 190° C.). In some embodiments, the Tg is up to about 200° C. In some embodiments, the Tg is up to about 130° C. (e.g., at least about 110° C., at least about 111° C., at least about 112° C., at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 1216° C., at least about 127° C., at least about 128° C., at least about 129° C., or at least about 130° C.). Unless otherwise noted, the glass transition temperatures disclosed herein are measured under dry conditions.

In some embodiments the solid dispersion has a higher glass transition temperature than the glass transition temperature of amorphous COMPOUND 2, without being in the presence of the polymer(s). In some embodiments, the solid dispersion has a relaxation rate that is lower than the relaxation rate of amorphous COMPOUND 2, without being in the presence of the polymer(s).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hpromellose acetate succinate, (HPMCAS), hydroxypropylcellulose (HPC)), ethylcellulose, or cellulose acetate phthalate; polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit® E); cyclodextrins (e.g., .beta.-cyclodextrin); Poly (D, L-lactide) (PLA), Poly (D,L-lactide, co-glycolide acid (PLGA); and copolymers and derivatives thereof, including for example polyvinylpyrrollidone-vinyl acetate (PVP-VA), Polyvinyl caprolactam-polyvinyl, and acetate-polyethyleneglycol copolymer, Methylacrylate/methacrylic acid copolymer; Soluplus; Copovidone; and mixtures thereof.

In some embodiments, the solid dispersion includes one water-soluble polymer. In some embodiments, the solid dispersion includes one partially water-soluble polymer. In some embodiments, the polymer is a cellulose polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer(s) is polyvinylpyrrolidone (PVP).

In some embodiments, the one or more polymer(s) is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer(s) is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer(s) is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the polymer(s) is present in the solid dispersion in an amount of from about 30% w/w to about 70% w/w. In some embodiments, the polymer(s) is present in the solid dispersion in an amount of from about 35% w/w to about 65% w/w. In some embodiments, the polymer(s) is present in the solid dispersion in an amount of from about 40% w/w to about 60% w/w. In some embodiments, the polymer(s) is present in the solid dispersion in an amount of from about 45% w/w to about 55% w/w. In some embodiments, the polymer(s) is present in the solid dispersion in an amount of about 50% w/w.

In some embodiments, COMPOUND 2, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, COMPOUND 2, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, COMPOUND 2, is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, COMPOUND 2, is present in the solid dispersion in an amount of from about 30% w/w to about 70% w/w. In some embodiments, COMPOUND 2, is present in the solid dispersion in an amount of from about 35% w/w to about 65% w/w. In some embodiments, COMPOUND 2, is present in the solid dispersion in an amount of from about 40% w/w to about 60% w/w. In some embodiments, COMPOUND 2, is present in the solid dispersion in an amount of from about 45% w/w to about 55% w/w. In some embodiments, COMPOUND 2, is present in the solid dispersion in an amount of about 50% w/w.

In another embodiment, the solid dispersion includes about 20% w/w to about 80% w/w COMPOUND 2, and about 20% w/w to about 80% of polymer(s). In another embodiment, the solid dispersion includes about 25% w/w to about 75% w/w COMPOUND 2, and about 25% w/w to about 75% of polymer(s). In another embodiment, the solid dispersion includes about 30% w/w to about 70% w/w COMPOUND 2, and about 30% w/w to about 70% of polymer(s). In another embodiment, the solid dispersion includes about 35% w/w to about 65% w/w COMPOUND 2, and about 35% w/w to about 65% of polymer(s). In another embodiment, the solid dispersion includes about 40% w/w to about 60% w/w COMPOUND 2, and about 40% w/w to about 60% of polymer(s). In another embodiment, the solid dispersion includes about 45% w/w to about 55% w/w COMPOUND 2, and about 45% w/w to about 55% of polymer(s). In another embodiment, the solid dispersion includes about 50% w/w COMPOUND 2, and about 50% w/w of polymer(s).

In another embodiment, the solid dispersion includes about 45% w/w to about 55% w/w COMPOUND 2, and about 45% w/w to about 55% w/w HPMCAS (e.g., HPMCAS-MG or HPMCAS-HG, or other grades such as LF, MF, HF, or LG) or PVAP. In another embodiment, the solid dispersion includes about 50% w/w COMPOUND 2, and about 50% w/w of HPMCAS.

In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

Processes for Preparing Solid Dispersions

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising COMPOUND 2, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Spray drying converts a liquid feed to a dried particulate form. Spray drying generally involves the atomization of a liquid feed solution into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

Optionally, a secondary drying process such as fluidized bed drying or vacuum drying, may be used to reduce residual solvents (and other additives, such as glacial acetic acid) to pharmaceutically acceptable levels. Typically, spray-drying involves contacting a highly dispersed liquid suspension or solution (e.g., atomized solution), and a sufficient volume of hot air or gas (e.g., nitrogen, e.g., pure nitrogen) to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air (or into gas, e.g., nitrogen) that evaporates the solvent and conveys the dried product to a collector (e.g., a cyclone). The spent air or gas is then exhausted with the solvent (or solvent mixture including any additives such as glacial acetic acid), (e.g., then filtered) or alternatively the spent air or gas is sent to a condenser to capture and potentially recycle the solvent or solvent mixture. For example, if a gas (e.g., nitrogen) is used, the gas is then optionally recycled, heated again and returned to the unit in a closed loop system. Commercially available types of apparatus may be used to conduct the spray-drying. For example, commercial spray dryers are manufactured by Buchi Ltd. and Niro (e.g., the PSD line of spray driers manufactured by Niro).

Spray-drying typically employs solids loads of material from about 1% to about 30% or up to about 50% (i.e., therapeutically active compound plus and excipients), preferably at least about 10%. In some embodiments, solids loads of less than 10% may result in poor yields and unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 70° C. to about 150° C., preferably from about 40° C. to about 60° C., about 50° C. to about 55° C., or about 80° C. to about 110° C., e.g., about 90° C. The spray-drying is generally conducted with an outlet temperature of from about 20° C. to about 100° C., for example from about 25° C. to about 30° C. (e.g., about 26° C.), about 40° C. to about 50° C., about 50° C. to about 65° C., e.g., about 56° C. to about 58° C.

Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray-drying is fluidized spray drying (FSD). The steps in FSD can include, for example: preparing a liquid feed solution (e.g., containing COMPOUND 2, and optionally a polymer(s) and/or surfactant(s), dissolved or suspended in solvent(s)); atomizing (e.g., with a pressure nozzle, a rotary atomizer or disk, two-fluid nozzle or other atomizing methods) the feed solution upon delivery into the drying chamber of a spray dryer, e.g., operating in FSD mode; drying the feed solution in the drying chamber with heated air or a heated gas (e.g., nitrogen) to obtain a product, wherein larger particles of product separate out, e.g., drop out, while fines are carried by a stream of air or gas up to the top of the drying chamber (e.g., by natural convection) and to a cyclone, and re-introducing (e.g., at the top of the drying chamber or axially to the middle of the chamber) the fines into the drying chamber, wherein the re-introduced fines can agglomerate with newly formed product to generate an agglomerated product, wherein if the agglomerated product is large enough, it will separate out, if it is not large enough to separate out, the agglomerated product will be carried by convection to the top of the chamber and to the cyclone and re-introduced into the chamber. This process repeats until an agglomerated product that is large enough to drop out is formed. The fines can be re-introduced from the cyclone to the drying chamber via a feed pipe.

In some embodiments, rather than drying the feed solution with heated air or a heated gas, the feed solution can instead be spray congealed, e.g., the chamber is at room temperature (e.g., 21±4° C.) or is cooled, e.g., cooled gas (e.g., nitrogen) is used for the process.

FSD can further include collecting the agglomerated product in a first fluidizing chamber; which can be followed by discharging the agglomerated product from the first fluidizing chamber to a second fluidizing chamber, wherein a post-drying process can occur.

The agglomerated product (e.g., that separates out in the drying chamber) can then be transferred from the second fluidizing chamber to a third fluidizing chamber, where the agglomerated product is cooled. The agglomerated product (e.g., a solid dispersion of an amorphous compound) can then be further processed. For example, the product can be directly compressed. The product can optionally be blended with a surfactant, excipient, or pharmaceutically acceptable carrier, e.g., prior to direct compression. The product can optionally be further processed, e.g., milled, granulated, blended, and/or mixed with a melt granulate, surfactant, excipient, and/or pharmaceutically acceptable carrier.

FSD can be performed in a commercial spray dryer operating in fluidized spray dryer mode (FSD mode). FSD can be accomplished in either open cycle mode or closed cycle mode (e.g., the drying gas, e.g., nitrogen, is recycled). Examples of suitable spray dryers for use in FSD include dryers from Niro (e.g., the PSD line of spray driers manufactured by Niro: PHARMASD™; Chemical or SD line dryers). FSD can essentially be performed in any spray dryer that is configured to allow for the re-introduction of fines into the drying chamber.

Additional post drying, e.g., in a vacuum or fluidized bed dryer or a double cone or biconical post-dryer or a tumble dryer, can be performed if needed/applicable to remove further solvents. In some embodiments, a post-drying step is performed.

To remove the solvent or solvent mixture, vacuum drying, spray drying, fluidized spray drying, tray drying, lyophilization, rotovapping, and other drying procedures may be applied. Applying any of these methods using appropriate processing parameters, according to this disclosure, would provide COMPOUND 2 in an amorphous state in the final solid dispersion product. Upon use of appropriate conditions (e.g., low outlet temperatures in the spray dryer, use of low boiling point solvents, use of heated gas) that result in a dispersion, e.g., powder, with desirable properties (e.g., median particle size (d50) of 40-200 microns 9 e.g., 40-150 microns), powder bulk density of >0.2 g/ml (e.g., 0.2 to 0.5 g/ml), or >0.25 g/ml, improved powder flowability (e.g., low cohesion forces, low interparticle internal friction); and/or dry powder with low OVIs (Organic Volatile Impurities), e.g., below ICH limits and/or user specifications), the dispersion can be directly compressed into a dosage form.

In some embodiments, the inlet temperature is between about 50° C. and about 200° C., e.g., between about 60° C. and about 150° C., between about 70° C. and about 100° C., between about 60° C. and about 95° C., between about 65° C. and about 85° C., between about 70° C. and about 90° C., between about 85° C. and about 95° C., or between about 70° C. and about 85° C.

In some embodiments, the outlet temperature is between about room temperature (e.g., USP room temperature (e.g., 21±4° C.)) and about 80° C., e.g., between about 25° C. and about 75° C., between about 30° C. and about 65° C., between about 35° C. and about 70° C., between about 40° C. and about 65° C., between about 45° C. and about 60° C., between about 35° C. and about 45° C., between about 35° C. and about 40° C., or between about 37° C. and about 40° C.

In some embodiments, the temperature set points of the fluidized beds (the temperature for each bed being selected independently from the temperature selected for another bed) is between about room temperature (e.g., USP room temperature (e.g., 21±4° C.)) and about 100° C., e.g., between about 30° C. and about 95° C., between about 40° C. and about 90° C., between about 50° C. and about 80° C., between about 60° C. and about 85° C., between about 65° C. and about 95° C., or between about 80° C. and about 95° C.

FSD can be performed on a mixture containing COMPOUND 2. For example, FSD can be performed on a mixture containing COMPOUND 2, and one or more polymer(s), and optionally one or more surfactant(s), and optionally one or more additional excipients(s)) to obtain a solid dispersion of amorphous COMPOUND 2 thereof, e.g., that can be directly compressed into an oral dosage form (e.g., tablet). Alternatively, the dispersion can be blended with one or more excipients prior to compression.

In one embodiment, the process for preparing a solid dispersion of COMPOUND 2 comprises:
a) forming a mixture of COMPOUND 2, one or more polymer(s), and one or more solvent(s); and
b) rapidly removing the solvent(s) from the solution to form a solid amorphous dispersion comprising COMPOUND 2 and the one or more polymer(s). The one or more polymer(s) and one or more solvent(s) may be any of those disclosed herein.

In some embodiments, the solvent is removed by spray drying. In some embodiments the solid dispersion is tray dried using a convection tray dryer. In some embodiments, the solid dispersion is screened.

In one embodiment, COMPOUND 2 is crystalline. In another embodiment, COMPOUND 2 is amorphous.

As would be appreciated by one of skill in the art, spray drying may be done and is often done in the presence of an inert gas such as nitrogen. In certain embodiments, processes that involve spray drying may be done in the presence of a supercritical fluid involving carbon dioxide or a mixture including carbon dioxide.

In another embodiment, the process for preparing a solid dispersion of COMPOUND 2 comprises:
a) forming a mixture of COMPOUND 2, a polymer, and a solvent; and
b) spray-drying the mixture to form a solid dispersion comprising COMPOUND 2 and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein.

In some embodiments, the solvent comprises one or more volatile solvent(s) to dissolve or suspend COMPOUND 2 and the polymer(s). In some embodiments, the one or more solvent(s) completely dissolves COMPOUND 2 and the polymer(s).

In some embodiments, the one or more solvent(s) is a volatile solvent (e.g., methylene chloride, acetone, methanol, ethanol, chloroform, tetrahydrofuran (THF), or a mixture thereof). Examples of suitable volatile solvents include those that dissolve or suspend the therapeutically active compound either alone or in combination with another co-solvent. In some embodiments, the solvent(s) completely dissolves the therapeutically active compound. In some embodiments, the solvent is acetone. In some embodiments, the solvent is methanol.

In some embodiments, the solvent is a non-volatile solvent (e.g., organic acids such as glacial acetic acid, dimethyl sulfoxide (DMSO), dimethylformamide (DMF), or water). In some embodiments, a non-volatile solvent is a component in a solvent system. For example the non-volatile solvent is present as a component in a solvent from about 1% to about 20% w/w (e.g., from about 3% w/w to about 15% w/w, from about 4% w/w to about 12% w/w, or from about 5% w/w to about 10% w/w).

In some embodiments, the solvent is a mixture of solvents. For example, the solvent can include from about 0% to about 30% acetone and from about 70% to about 100% methanol, or the solvent can include from about 0% to about 40% acetone and from about 60% to about 100% methanol. Other exemplary ratios of methanol to acetone include 80:20, 75:25, 70:30, 60:40, 55:45, and 50:50.

In some embodiments, the solvent is a combination of solvents including at least one non-volatile solvent. For example, the solvent is a combination of components that includes both a volatile solvent and a non-volatile solvent. In some embodiments, the solvent system is a combination of a volatile solvent or combination of solvents such as methanol and acetone with a non-volatile solvent such as glacial acetic acid. For example, the solvent system comprises from about 40% to about 80% methanol, from about 20% to about 35% acetone, and from about 1% to about 15% glacial acetic acid (e.g., from about 50% to about 70% methanol, from about 25% to about 30% acetone, and from about 3% to about 12% glacial acetic acid).

In some embodiments, the solvent system is a combination of a volatile solvent or combination of solvents such as methanol and acetone with a non-volatile solvent such as water. For example, the solvent system comprises from about 40% to about 80% methanol, from about 20% to about 35% acetone, and from about 0.1% to about 15% water (e.g., from about 50% to about 70% methanol, from about 25% to about 30% acetone, and from about 1% to about 5% water).

In certain embodiments, the pharmaceutical compositions of the solid dispersion may be made by a process described herein. For example, a solid dispersion of: (a) COMPOUND 2 and (b) one or more polymer(s), and optionally one or more surfactant(s) and optionally one or more additional excipient(s).

A. Pharmaceutical Compositions Containing Solid Dispersions of COMPOUND 2

In certain embodiments, provided herein are pharmaceutical compositions, comprising: (a) a solid dispersion, comprising COMPOUND 2 and a polymer; and (b) one or more pharmaceutically acceptable carrier(s). Examples of pharmaceutically acceptable carriers are fillers, disintegrants, wetting agents, glidants, and lubricants.

In some embodiments, the pharmaceutical compositions may be orally administered in any orally acceptable dosage form including, but not limited to, capsules, tablets, emulsions and aqueous suspensions, dispersions and solutions.

In some embodiments the pharmaceutical composition is a tablet.

In some embodiments the pharmaceutical composition comprises a directly compressed dosage form of COMPOUND 2.

In some embodiments, the pharmaceutical composition also includes a filler. The filler can be, for example, microcrystalline cellulose, lactose, mannitol, ethyl cellulose, sorbitol, starch, sucrose, calcium phosphate, powdered cellulose, silicified microcrystalline cellulose, isomalt, or mixtures thereof. In some embodiments, the filler is microcrystalline cellulose.

In some embodiments, the filler is present in the pharmaceutical composition in an amount of between about 10% w/w and 50% w/w (e.g., between about 15% w/w and about 45% w/w; between about 20% w/w and about 40% w/w; between about 25% w/w and about 35% w/w; or between about 28% w/w and about 32% w/w). In some embodiments, the filler is present in the pharmaceutical composition in an amount of from about 20% w/w to about 35% w/w, for example from about 25% w/w to about 34% w/w, or from about 26% w/w to about 33% w/w, or from about 27% w/w to about 32% w/w, for example, about 28% w/w, about 28.5% w/w, about 29% w/w, about 29.5% w/w about 30% w/w, about 30.5% w/w, about 31% w/w, or about 31.5% w/w. In some embodiments, the filler is present in the pharmaceutical composition in an amount of about 29% w/w, about 29.1% w/w, about 29.2% w/w, about 29.3% w/w, about 29.4% w/w, about 29.5% w/w, about 29.6% w/w, about 29.7% w/w, about 29.8% w/w, about 29.9% w/w, or about 30% w/w. In some embodiments, the filler is present in the pharmaceutical composition in an amount of between about 25% w/w and about 35% w/w. In some embodiments, the filler is present in the pharmaceutical composition in an amount of about 29.5% w/w.

In some embodiments, the pharmaceutical composition also includes a disintegrant. The disintegrant can be, for example, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, or mixtures thereof. In some embodiments, the disintegrant is croscarmellose sodium.

In some embodiments, the disintegrant is present in the pharmaceutical composition in an amount of between about 1% w/w and 15% w/w (e.g., between about 3% w/w and about 12% w/w; between about 4% w/w and about 10% w/w; between about 5% w/w and about 7% w/w; or between about 6% w/w and about 7% w/w). In some embodiments, the disintegrant is present in the pharmaceutical composition in an amount of about 3% w/w, about 3.5% w/w, about 4% w/w, about 49.5% w/w about 5% w/w, about 5.5% w/w, about 6% w/w, or about 6.5% w/w, about 7% w/w, about 7.5% w/w, about 8% w/w, about 8.5% w/w, about 9% w/w, about 9.5% w/w, or about 10% w/w. In some embodiments, the disintegrant is present in the pharmaceutical composition in an amount of between about 5% w/w and about 7% w/w. In some embodiments, the disintegrant is present in the pharmaceutical composition in an amount of about 6% w/w.

In some embodiments, the pharmaceutical composition also includes a wetting agent. The wetting agent can be, for example, sodium lauryl sulfate, sodium dodecyl sulfate, polysorbates (such as Tween 20 and Tween 80), poloxamers (such as Poloxamer 335 and Poloxamer 407), glyceryl monooleate, or mixtures thereof. In some embodiments, the wetting agent is sodium lauryl sulfate.

In some embodiments, the wetting agent is present in the pharmaceutical composition in an amount of between about 0.1% w/w and 2% w/w (e.g., between about 0.5% w/w and about 2% w/w; between about 0.5% w/w and about 1.5% w/w; or between about 1% w/w and about 1.5% w/w). In some embodiments, the wetting agent is present in the pharmaceutical composition in an amount of about 0.1% w/w, about 0.2% w/w, about 0.3% w/w, about 0.4% w/w about 0.5% w/w, about 0.6% w/w, about 0.7% w/w, or about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2% w/w. In some embodiments, the wetting agent is present in the pharmaceutical composition in an amount of between about 0.5% w/w and about 1.5% w/w. In some embodiments, the wetting agent is present in the pharmaceutical composition in an amount of about 1% w/w.

In some embodiments, the pharmaceutical composition also includes a glidant. The glidant can be, for example, silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide.

In some embodiments, the glidant is present in the pharmaceutical composition in an amount of between about 0.1% w/w and 5% w/w (e.g., between about 1% w/w and about 4% w/w; between about 1% w/w and about 3% w/w; or between about 1.5% w/w and about 2.5% w/w). In some embodiments, the glidant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the glidant is present in the pharmaceutical composition in an amount of about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w. In some embodiments, the glidant is present in the pharmaceutical composition in an amount of between about 1% w/w and about 3% w/w. In some embodiments, the glidant is present in the pharmaceutical composition in an amount of about 2% w/w.

In some embodiments, the pharmaceutical composition also includes a lubricant. The lubricant can be, for example, magnesium stearate, talc, sodium stearyl fumarate, glyceryl behenate, hydrogenated vegetable oil, zinc stearate, calcium stearate, sucrose stearate, polyvinyl alcohol, magnesium lauryl sulfate, or mixtures thereof. In some embodiments, the lubricant is magnesium stearate.

In some embodiments, the lubricant is present in the pharmaceutical composition in an amount of between about 0.1% w/w and 5% w/w (e.g., between about 1% w/w and about 4% w/w; between about 1% w/w and about 3% w/w; or between about 1% w/w and about 2% w/w). In some embodiments, the lubricant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the lubricant is present in the pharmaceutical composition in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, or about 2.5% w/w. In some embodiments, the lubricant is present in the pharmaceutical composition in an amount of between about 0.5% w/w and about 2.5% w/w. In some embodiments, the lubricant is present in the pharmaceutical composition in an amount of about 1.5% w/w.

In some embodiments, the solid dispersion makes up about 25% to 85% by weight of the total weight of the pharmaceutical composition. In some embodiments, the solid dispersion makes up about 50% to about 70% by weight of the total weight of the pharmaceutical composition.

In some embodiments, the COMPOUND 2 makes up about 15% to 45% of the total weight of the pharmaceutical composition, and the one or more polymer(s) makes up about 15% to 45% of the total weight of the pharmaceutical composition.

In some embodiments, the COMPOUND 2 makes up about 20% w/w of the pharmaceutical composition, the one or more polymer(s) makes up about 40% w/w of the pharmaceutical composition.

In some embodiments, the COMPOUND 2 makes up about 25% w/w of the pharmaceutical composition, the one or more polymer(s) makes up about 35% w/w of the pharmaceutical composition.

In some embodiments, the COMPOUND 2 makes up about 30% w/w of the pharmaceutical composition, the one or more polymer(s) makes up about 30% w/w of the pharmaceutical composition.

In some embodiments, the COMPOUND 2 makes up about 35% w/w of the pharmaceutical composition, the one or more polymer(s) makes up about 25% w/w of the pharmaceutical composition.

In some embodiments, the solid dispersion makes up from between about 50% w/w to about 70% w/w of the pharmaceutical composition, the filler makes up from between about 25% w/w to about 35% w/w of the pharmaceutical composition, the disintegrant makes up from between about 5% w/w to about 7% w/w of the pharmaceutical composition, the wetting agent makes up from between about 0.5% w/w to about 1.5% w/w of the pharmaceutical composition, the glidant makes up from between about 1% w/w to about 3% w/w of the pharmaceutical composition, the lubricant makes up from between about 0.5% w/w to about 2.5% w/w of the pharmaceutical composition thereby totaling 100% by weight of the composition.

In some embodiments, the solid dispersion makes up about 60% w/w of the pharmaceutical composition, the filler makes up about 29.5% w/w of the pharmaceutical composition, the disintegrant makes up about 6% w/w of the pharmaceutical composition, the wetting agent makes up about 1% w/w of the pharmaceutical composition, the glidant makes up about 2% w/w of the pharmaceutical composition, the lubricant makes up about 1.5% w/w of the pharmaceutical composition.

In some embodiments, the pharmaceutical composition comprises, from between about 25% w/w to about 35% w/w of COMPOUND 2 from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and from between about 0.5% w/w to about 2.5% w/w of magnesium stearate, thereby totaling 100% by weight of the composition.

In some embodiments, the pharmaceutical composition comprises, about 30% w/w of COMPOUND 2 about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In some embodiments, the solid dispersion, filler, disintegrant, wetting agent, glidant, and lubricant are added intragranularly. In some embodiments, an additional amount of the filler, disintegrant, glidant, and lubricant are added extragranularly.

In some embodiments, the pharmaceutical composition comprises, the following intragranularly added components: the solid dispersion makes up from about 50% w/w to about 70% w/w of the pharmaceutical composition, the filler makes up from about 18% w/w to about 26% w/w of the pharmaceutical composition, disintegrant makes up from about 2% w/w to about 6% w/w of the pharmaceutical composition, wetting agent makes up from about 0.5% w/w to about 1.5% w/w of the pharmaceutical composition, glidant makes up from about 0.5% w/w to about 1.5% w/w of the pharmaceutical composition, and lubricant makes up from about 0.25% w/w to about 1% w/w of the pharmaceutical composition.

In some embodiments, the pharmaceutical composition comprises the following extragranularly added components: an additional amount of the filler makes up from about 4% w/w to about 12% w/w of the pharmaceutical composition, an additional amount of the disintegrant makes up from about 1% w/w to about 3% w/w of the pharmaceutical composition, an additional amount of the glidant makes up from about 0.5% w/w to about 1.5% w/w of the pharmaceutical composition, and an additional amount of the lubricant makes up from about 0.5% w/w to about 1.5% w/w of the pharmaceutical composition, and are added extragranularly.

In some embodiments, the pharmaceutical composition comprises, the following intragranularly added components: the solid dispersion makes up about 60% w/w of the pharmaceutical composition, the filler makes up about 21.5% w/w of the pharmaceutical composition, disintegrant makes up about 4% w/w of the pharmaceutical composition, wetting agent makes up about 1% w/w of the pharmaceutical composition, glidant makes up about 1% w/w of the pharmaceutical composition, and lubricant makes up about 0.5% w/w of the pharmaceutical composition.

In some embodiments, the pharmaceutical composition comprises the following extragranularly added components: an additional amount of the filler makes up about 8% w/w of the pharmaceutical composition, an additional amount of the disintegrant makes up about 2% w/w of the pharmaceutical composition, an additional amount of the glidant makes up about 1% w/w of the pharmaceutical composition, and an additional amount of the lubricant makes up about 1% w/w of the pharmaceutical composition, and are added extragranularly.

In some embodiments, the pharmaceutical composition comprises, the following intragranularly added components: the solid dispersion comprising COMPOUND 2 and hypromellose acetate succinate (HPMCAS), makes up from about 50% w/w to about 70% w/w of the pharmaceutical composition, microcrystalline cellulose makes up from about 18% w/w to about 26% w/w of the pharmaceutical composition, croscarmellose sodium makes up from about 2% w/w to about 6% w/w of the pharmaceutical composition, sodium lauryl sulfate makes up from about 0.5% w/w to about 1.5% w/w of the pharmaceutical composition, colloidal silicon dioxide makes up from about 0.5% w/w to about 1.5% w/w of the pharmaceutical composition, and magnesium stearate makes up from about 0.25% w/w to about 1% w/w of the pharmaceutical composition.

In some embodiments, the pharmaceutical composition comprises the following extragranularly added components: an additional amount of microcrystalline cellulose makes up from about 4% w/w to about 12% w/w of the pharmaceutical composition, an additional amount of croscarmellose sodium makes up from about 1% w/w to about 3% w/w of the pharmaceutical composition, an additional amount of colloidal silicon dioxide makes up from about 0.5% w/w to about 1.5% w/w of the pharmaceutical composition, and an additional amount of magnesium stearate makes up from about 0.5% w/w to about 1.5% w/w of the pharmaceutical composition, and are added extragranularly.

In some embodiments, the pharmaceutical composition comprises, the following intragranularly added components: the solid dispersion comprising COMPOUND 2 and hypromellose acetate succinate (HPMCAS), makes up about 60% w/w of the pharmaceutical composition, microcrystalline cellulose makes up about 21.5% w/w of the pharmaceutical composition, croscarmellose sodium makes up about 4% w/w of the pharmaceutical composition, sodium lauryl sulfate makes up about 1% w/w of the pharmaceutical composition, colloidal silicon dioxide makes up about 1% w/w of the pharmaceutical composition, and magnesium stearate makes up about 0.5% w/w of the pharmaceutical composition.

In some embodiments, the pharmaceutical composition comprises the following extragranularly added components: an additional amount of microcrystalline cellulose makes up about 8% w/w of the pharmaceutical composition, an additional amount of croscarmellose sodium makes up about 2% w/w of the pharmaceutical composition, an additional amount of colloidal silicon dioxide makes up about 1% w/w of the pharmaceutical composition, and an additional amount of magnesium stearate makes up about 1% w/w of the pharmaceutical composition, and are added extragranularly.

B. Pharmaceutical Compositions Containing Cytarabine

In certain embodiments, provided herein are pharmaceutical compositions comprising cytarabine and a pharmaceutically acceptable carrier for administration to a patient in need thereof in the methods provided herein. In certain embodiments, the pharmaceutical compositions comprising cytarabine are for parenteral administration. In one embodiment, the pharmaceutical composition comprises cytarabine in a sterile solution for intravenous, intrathecal or subcutaneous administration.

In certain embodiments, the pharmaceutical composition comprises an aqueous solution containing 20 mg/mL cytarabine. In certain embodiments, the pharmaceutical composition comprises an aqueous solution containing 100 mg/mL cytarabine.

In one embodiment, the pharmaceutical composition comprising cytarabine contains no preservative. In one embodiment, the pharmaceutical composition comprising cytarabine further comprises sodium chloride. In one embodiment, sodium chloride is present in about 0.68% based on total mass of the composition. In one embodiment, the pharmaceutical composition further comprises hydrochloric acid and/or sodium hydroxide to adjust the pH of the composition to about 7.2-7.8. In one embodiment, the pharmaceutical composition further comprises hydrochloric acid and/or sodium hydroxide to adjust the pH of the composition to about 7.3-7.7. In one embodiment, the pharmaceutical composition further comprises hydrochloric acid and/or sodium hydroxide to adjust the pH of the composition to about 7.4, 7.6 or 7.7.

In one embodiment, the pharmaceutical composition comprising cytarabine contains a preservative. In one embodiment, the preservative is benzyl alcohol. In one embodiment, the amount of benzyl alcohol is about 0.9% based on total mass of the composition. In one embodiment, the pharmaceutical composition further comprises hydrochloric acid and/or sodium hydroxide to adjust the pH of the composition to about 7.6.

In certain embodiments, provided herein is a powder comprising cytarabine, wherein the powder is suitable for reconstitution. In certain embodiments, the composition is reconstituted with water containing 0.9% m/v benzyl alcohol.

In certain embodiments, cytarabine is formulated and administered according to a package insert for cytarabine.

C. Pharmaceutical Compositions Containing Daunorubicin

In certain embodiments, provided herein are pharmaceutical compositions comprising daunorubicin hydrochloride and a pharmaceutically acceptable carrier. In certain embodiments, the compositions are for intravenous administration to a patient in need thereof in the methods provided herein. In certain embodiments, the compositions further comprise sodium chloride. In certain embodiments, the compositions further comprise sodium hydroxide and/or hydrochloric acid to adjust the pH to 3-7. In certain embodiments, the compositions have a pH in the range 3-4, 4-5 or 4.5-6.5. In certain embodiments, the compositions comprise an aqueous solution of daunorubicin hydrochloride equivalent to 5 mg/mL daunorubicin, 9 mg/mL sodium chloride, sodium hydroxide and/or hydrochloric acid to adjust pH to 3-4.

In certain embodiments, daunorubicin is formulated and administered per its package insert.

D. Pharmaceutical Compositions Containing Idarubicin

In certain embodiments, provided herein are pharmaceutical compositions comprising idarubicin hydrochloride and a pharmaceutically acceptable carrier. In certain embodiments, the compositions comprise idarubicin hydrochloride as a sterile lyophilized powder for reconstitution and intravenous administration. In certain embodiments, the compositions comprise sterile lyophilized powder of idarubicin hydrochloride in an amount of about 20 mg per single use vial. In certain embodiments, the compositions further comprise lactose NF.

In certain embodiments, provided herein are pharmaceutical compositions comprising idarubicin hydrochloride in a sterile, semi-synthetic, preservative-free solution for intravenous administration. In certain embodiments, provided herein are pharmaceutical compositions comprising idarubicin hydrochloride in isotonic parenteral preservative-free solution. In certain embodiment, the compositions are provided in single use vials.

In the one embodiment, the vials contain about 5 mL, 10 mL or 20 mL solution comprising idarubicin hydrochloride. In certain embodiments, each vial contains idarubicin hydrochloride in an amount 1 mg/mL and the following inactive ingredients: glycerin, USP 25 mg/mL, water, hydrochloric acid, NF to adjust the pH to about 3.5.

In certain embodiments, each vial contains about 5 mg idarubicin hydrochloride, 125 mg glycerol, water for injections q.s. to 5 mL and HCl to pH 3.5.

In certain embodiments, each vial contains about 10 mg idarubicin hydrochloride, 250 mg glycerol, water for injections q.s. to 10 mL and HCl to pH 3.5.

In certain embodiments, idarubicin is formulated and administered per its package insert.

E. Pharmaceutical Compositions Containing Etoposide

In certain embodiments, provided herein are pharmaceutical compositions comprising etoposide phosphate and a pharmaceutically acceptable carrier. In certain embodiments, the pharmaceutical compositions of etoposide phosphate are for intravenous infusion. In one embodiment, the pharmaceutical composition is provided in a single-dose vial containing etoposide phosphate equivalent to about 100 mg etoposide, about 32.7 mg sodium citrate USP, and about 300 mg dextran 40.

In certain embodiments, the pharmaceutical compositions of etoposide phosphate are for intravenous injection. In one embodiment, the pharmaceutical compositions are provided as 20 mg/mL solutions in 100 mg (5 mL), 200 mg (10 mL) or 500 mg (25 mL) sterile, multiple dose vials, each mL containing about 20 mg etoposide, about 2 mg citric acid, about 80 mg polysorbate 80, about 650 mg polyethylene glycol 300, and dehydrated alcohol about 33.2% (v/v).

In certain embodiments, etoposide is formulated and administered per its package insert.

F. Pharmaceutical Compositions Containing Mitoxantrone

In certain embodiments, provided herein are pharmaceutical compositions comprising mitoxantrone hydrochloride and a pharmaceutically acceptable carrier. In certain embodiments, the pharmaceutical compositions of mitoxantrone hydrochloride are for intravenous administration.

In certain embodiments, the compositions are provided as a concentrate that requires dilution prior to injection. In certain embodiments, the composition is a sterile aqueous solution comprising mitoxantrone hydrochloride equivalent to 2 mg/mL mitoxantrone free base, sodium chloride (about 0.80% w/v), sodium acetate (about 0.005% w/v), glacial acetic acid (about 0.046% w/v), and water. In one embodiment, the composition has a pH of 3.0 to 4.5 and contains 0.14 mEq of sodium per mL. In certain embodiments, the composition does not contain any preservative.

In certain embodiments, mitoxantrone is formulated and administered per its package insert.

Methods of Use

In one embodiment, provided herein are methods of treating acute myeloid leukemia (AML), characterized by the presence of a mutant allele of IDH1, by administering to a subject a combination of a mutant IDH1 inhibitor and an AML induction and consolidation therapy.

In one embodiment, the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, or a pharmaceutically acceptable salt, solvate, tautomer, stereoisomer, isotopologue, prodrug, or a polymorph thereof (COMPOUND 2).

In one embodiment, provided herein is a method of treating AML characterized by the presence of a mutant allele of IDH1, comprising administering to a subject a therapeutically effective amount of COMPOUND 2 and the AML induction therapy and consolidation therapy.

In one embodiment, provided herein is a method of treating AML characterized by the presence of a mutant allele of IDH1, comprising administering to a subject a pharmaceutical composition comprising a therapeutically effective amount of COMPOUND 2 and the AML induction therapy and consolidation therapy.

In one embodiment, provided herein is a method of treating AML selected from newly diagnosed AML, previously untreated AML, AML arising from myelodysplastic syndrome (MDS), AML arising from antecedent hematologic disorder (AHD) and AML arising after exposure to genotoxic injury. In certain embodiments, the genotoxic injury is resulting from radiation and/or chemotherapy. In one embodiment, provided herein is a method of treating AML arising after exposure to genotoxic injury resulting from radiation and/or chemotherapy.

In one embodiment, provided herein is a method of treating newly diagnosed AML.

In one embodiment, provided herein is a method of treating previously untreated AML.

In one embodiment, provided herein is a method of treating AML arising from myelodysplastic syndrome (MDS).

In one embodiment, provided herein is a method of treating AML arising from antecedent hematologic disorder (AHD).

In one embodiment, provided herein is a method of treating AML arising after exposure to genotoxic injury.

In one embodiment, the AML induction therapy is a combination of cytarabine and daunorubicin. In one embodiment, the AML induction therapy is a combination of cytarabine and idarubicin.

In one embodiment, the AML consolidation therapy is cytarabine. In one embodiment, the AML consolidation therapy is a combination of mitoxantrone and etoposide.

In one embodiment, the method of treating AML provided herein comprises administering a therapeutically effective amount of COMPOUND 2 orally and cytarabine and daunorubicin intravenously during the induction stage, followed by administering a therapeutically effective amount of COMPOUND 2 orally and cytarabine intravenously during the consolidation stage.

In one embodiment, the method of treating AML provided herein comprises administering a therapeutically effective amount of COMPOUND 2 orally and cytarabine and idarubicin intravenously during the induction stage, followed by administering a therapeutically effective amount of COMPOUND 2 orally and cytarabine intravenously during the consolidation stage.

In one embodiment, the method of treating AML provided herein comprises administering a therapeutically effective amount of COMPOUND 2 orally and cytarabine and daunorubicin intravenously during the induction stage followed by administering mitoxantrone and etoposide intravenously during the consolidation stage.

In one embodiment, the method of treating AML provided herein comprises administering a therapeutically effective amount of COMPOUND 2 orally and cytarabine and idarubicin intravenously during the induction stage, followed by administering a therapeutically effective amount of COMPOUND 2 orally and mitoxantrone and etoposide intravenously during the consolidation stage.

In one embodiment, COMPOUND 2, cytarabine, and daunorubicin are administered concurrently. In one embodiment, COMPOUND 2, cytarabine, and daunorubicin are administered sequentially. In one embodiment, COMPOUND 2, cytarabine, and idarubicin are administered concurrently. In one embodiment, COMPOUND 2, cytarabine, and idarubicin are administered sequentially.

In one embodiment, the malignancy to be treated is characterized by a mutant allele of IDH1, wherein the IDH1 mutation results in a new ability of the enzyme to catalyze the NAPH dependent reduction of α ketoglutarate to R(-)-2 hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

A malignancy can be analyzed by sequencing cell samples to determine the presence and specific nature of (e.g., the changed amino acid present at) a mutation at amino acid 132 of IDH1.

Without being bound by theory, applicants have found that mutant alleles of IDH1, wherein the IDH1 mutation results in a new ability of the enzyme to catalyze the NAPH dependent reduction of α ketoglutarate to R(-)-2 hydroxyglutarate, and in particular R132H mutations of IDH1, characterize a subset of all types of cancers, without regard to their cellular nature or location in the body. Thus, the compounds, compositions and methods provided herein are useful to treat any type of cancer that is characterized by the presence of a mutant allele of IDH1 imparting such activity and in particular an IDH1 R132H or R132C mutation.

In one embodiment the malignancy is a tumor wherein at least 30, 40, 50, 60, 70, 80 or 90% of the tumor cells carry an IDH1 mutation, and in particular an IDH1 R132H or R132C mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 2. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well known determinations of efficacy of malignancy treatment, such as reduction in number and size of tumors and/or other cancer associated lesions, improvement in the general health of the subject, and alterations in other biomarkers that are associated with malignancy treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at 80 degrees Celsius prior to LC MS/MS to assess 2 hydroxyglutarate levels. A variety of different liquid chromatography (LC) separation methods can be used. Each method can be coupled by negative electrospray ionization (ESI, 3.0 kV) to triple quadrupole mass spectrometers operating in multiple reaction monitoring (MRM) mode, with MS parameters optimized on infused metabolite standard solutions. Metabolites can be separated by reversed phase chromatography using 10 mM tributyl amine as an ion pairing agent in the aqueous mobile phase, according to a variant of a previously reported method (Luo et al. J Chromatogr A 1147, 153 64, 2007). One method allows resolution of TCA metabolites: t=0, 50% B; t=5, 95% B; t=7, 95% B; t=8, 0% B, where B refers to an organic mobile phase of 100% methanol. Another method is specific for 2 hydroxyglutarate, running a fast linear gradient from 50% 95% B (buffers as defined above) over 5 minutes. A Synergi Hydro RP, 100 mm×2 mm, 2.1 µm particle size (Phenomonex) can be used as the column, as described above. Metabolites can be quantified by comparison of peak areas with pure metabolite standards at known concentration. Metabolite flux studies from 13C glutamine can be performed as described, e.g., in Munger et al. Nat Biotechnol 26, 1179 86, 2008.

In one embodiment, 2HG is directly evaluated.

In another embodiment, a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

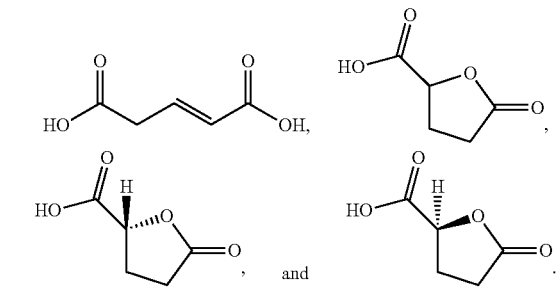

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Thus, according to another embodiment, provided herein is a method of treating 2-hydroxyglutaric aciduria, particularly D-2-hydroxyglutaric aciduria, in a subject by administering to the subject COMPOUND 2, cytarabine, and daunorubicin. In one embodiment, provided herein is a method of treating 2 hydroxyglutaric aciduria, particularly D-2-hydroxyglutaric aciduria, in a subject by administering to the subject COMPOUND 2, cytarabine, and idarubicin.

In one embodiment, prior to and/or after treatment with COMPOUND 2, cytarabine, and daunorubicin, the method further comprises the step of evaluating the growth, size, weight, invasiveness, stage and/or other phenotype of the malignancy. In one embodiment, prior to and/or after treatment with COMPOUND 2, cytarabine, and idarubicin, the method further comprises the step of evaluating the growth, size, weight, invasiveness, stage and/or other phenotype of the malignancy.

In one embodiment, prior to and/or after treatment with COMPOUND 2, cytarabine, and daunorubicin, the method further comprises the step of evaluating the IDH1 genotype of the malignancy. In one embodiment, prior to and/or after treatment with COMPOUND 2, cytarabine, and idarubicin, the method further comprises the step of evaluating the IDH1 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 2, cytarabine, and daunorubicin, the method further comprises the step of determining the 2HG level in the subject. In one embodiment, prior to and/or after treatment with COMPOUND 2, cytarabine, and idarubicin, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one embodiment, depending on the disease to be treated and the subject's condition, COMPOUND 2 may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. COMPOUND 2 may be formulated in suitable dosage unit with pharmaceutically acceptable excipients, carriers, adjuvants and vehicles, appropriate for each route of administration. In one embodiment, COMPOUND 2 is administered orally.

In one embodiment, the amount of COMPOUND 2 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 2 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 2 can be delivered as a single dose such as, e.g., a single bolus injection, or oral tablets or pills; or over time such as, e.g., continuous infusion over time or divided bolus doses over time. In one embodiment, COMPOUND 2 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 2 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 2 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 2 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In one embodiment, depending on the disease to be treated and the subject's condition, cytarabine may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. cytarabine may be formulated in suitable dosage unit with pharmaceutically acceptable excipients, carriers, adjuvants and vehicles, appropriate for each route of administration. In one embodiment, cytarabine is administered intravenously.

In certain embodiments, treatment cycles comprise multiple doses of cytarabine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of cytarabine administered to a subject in need thereof over 2 to 10 days. In one embodiment, treatment cycles comprise multiple doses of cytarabine administered to a subject in need thereof over 4 to 8 days. In one embodiment, treatment cycles comprise multiple doses of cytarabine administered to a subject in need thereof for 4 days. In one embodiment, treatment cycles comprise multiple doses of cytarabine administered to a subject in need thereof for 5 days. In one embodiment, treatment cycles comprise multiple doses of cytarabine administered to a subject in need thereof for 6 days. In one embodiment, treatment cycles comprise multiple doses of cytarabine administered to a subject in need thereof for 7 days. In one embodiment, treatment cycles comprise multiple doses of cytarabine administered to a subject in need thereof for 8 days. In one embodiment, treatment cycles comprise multiple doses of cytarabine administered to a subject in need thereof for 9 days. In one embodiment, treatment cycles comprise multiple doses of cytarabine administered to a subject in need thereof for 10 days.

Suitable dosage amounts for the methods provided herein include, e.g., therapeutically effective amounts and prophylactically effective amounts of cytarabine. For example, in certain embodiments, the amount of cytarabine administered during the induction stage in the methods provided herein may range, e.g., between about 10 mg/m$^2$/day and about 1,500 mg/m$^2$/day. In certain embodiments, the amount of cytarabine is between about 50 mg/m$^2$/day and about 1,000 mg/m$^2$/day. In certain embodiments, the amount of cytarabine is between about 100 mg/m$^2$/day and about 500 mg/m$^2$/day. In certain embodiments, the amount of cytarabine is between about 150 mg/m$^2$/day and about 300 mg/m$^2$/day. In certain embodiments, the amount of cytarabine is between about 150 mg/m$^2$/day and about 200 mg/m$^2$/day. In certain embodiments, the particular dosage is about 50 mg/m$^2$/day. In one embodiment, the particular dosage is about 75 mg/m$^2$/day. In one embodiment, the particular dosage is about 100 mg/m$^2$/day. In one embodiment, the particular dosage is about 125 mg/m$^2$/day. In one embodiment, the particular dosage is about 150 mg/m$^2$/day. In one embodiment, the particular dosage is about 175 mg/m$^2$/day. In one embodiment, the particular dosage is about 200 mg/m$^2$/day. In one embodiment, the particular dosage is about 225 mg/m$^2$/day. In one embodiment, the particular dosage is about 250 mg/m$^2$/day. In one embodiment, the particular dosage is about 275 mg/m$^2$/day. In one embodiment, the particular dosage is about 300 mg/m$^2$/day. In one embodiment, the particular dosage is about 350 mg/m$^2$/day. In one embodiment, the particular dosage is about 400 mg/m$^2$/day. In certain embodiments, the particular dosage is up to about 100 mg/m$^2$/day. In one embodiment, the particular dosage is up to about 125 mg/m$^2$/day. In one embodiment, the particular dosage is up to about 150 mg/m$^2$/day. In one embodiment, the particular dosage is up to about 175 mg/m$^2$/day. In one embodiment, the particular dosage is up to about 200 mg/m$^2$/day. In one embodiment, the particular dosage is up to about 225 mg/m$^2$/day. In one embodiment, the particular dosage is up to about 250 mg/m$^2$/day. In one embodiment, the particular dosage is up to about 275 mg/m$^2$/day. In one embodiment, the particular dosage is up to about 300 mg/m$^2$/day. In one embodiment, the particular dosage is up to about 350 mg/m$^2$/day. In one embodiment, the particular dosage is up to about 400 mg/m$^2$/day.

In certain embodiments, the amount of cytarabine administered during the consolidation stage in the methods provided herein may range, e.g., between about 0.1 g/m$^2$/day and about 25 g/m$^2$/day. For example, in certain embodiments, the amount of cytarabine administered in the methods provided herein may range, e.g., between about 0.5 g/m$^2$/day and about 15 g/m$^2$/day. In certain embodiments, the amount of cytarabine is between about 1 g/m$^2$/day and about 10 g/m$^2$/day. In certain embodiments, the amount of cytarabine is between about 1 g/m$^2$/day and about 5 g/m$^2$/day. In certain embodiments, the amount of cytarabine is between about 1 g/m$^2$/day and about 3 g/m$^2$/day. In certain embodiments, the amount of cytarabine is between about 1 g/m$^2$/day and about 2 g/m$^2$/day. In certain embodiments, the amount of cytarabine is between about 1 g/m$^2$/day and about 1.5 g/m$^2$/day. In certain embodiments, the amount of cytarabine is between about 2 g/m$^2$/day and about 3 g/m$^2$/day. In certain embodiments, the particular dosage of cytarabine is about 0.1 g/m$^2$/day. In one embodiment, the particular dosage is about 0.5 g/m$^2$/day. In one embodiment, the particular dosage is about 1 g/m$^2$/day. In one embodiment, the particular dosage is about 1.5 g/m$^2$/day. In one embodiment, the particular dosage is about 2 g/m$^2$/day. In one embodiment, the particular dosage is about 2.5 g/m$^2$/day. In one embodiment, the particular dosage is about 3 g/m$^2$/day. In one embodiment, the particular dosage is about 4 g/m$^2$/day. In one embodiment, the particular dosage is about 5 g/m$^2$/day. In certain embodiments, the particular dosage of cytarabine is up to about 0.1 g/m$^2$/day. In one embodiment, the particular dosage is up to about 0.5 g/m$^2$/day. In one embodiment, the particular dosage is up to about 1 g/m$^2$/day. In one embodiment, the particular dosage is up to about 1.5 g/m$^2$/day. In one embodiment, the particular dosage is up to about 2 g/m$^2$/day. In one embodiment, the particular dosage is up to about 2.5 g/m$^2$/day. In one embodiment, the particular dosage is up to about 3 g/m$^2$/day. In one embodiment, the particular dosage is up to about 4 g/m$^2$/day. In one embodiment, the particular dosage is up to about 5 g/m$^2$/day.

In one embodiment, depending on the disease to be treated and the subject's condition, daunorubicin may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Daunorubicin may be formulated in suitable dosage unit with pharmaceutically acceptable excipients, carriers, adjuvants and vehicles, appropriate for each route of administration. In one embodiment, daunorubicin is administered intravenously.

In certain embodiments, treatment cycles comprise multiple doses of daunorubicin administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of daunorubicin administered to a subject in need thereof over 1 to 8 days. In one embodiment, treatment cycles comprise multiple doses of daunorubicin administered to a subject in need thereof over 2 to 6 days. In one embodiment, treatment cycles comprise multiple doses of daunorubicin administered to a subject in need thereof for 2 days. In one embodiment, treatment cycles comprise multiple doses of daunorubicin administered to a subject in need thereof for 3 days. In one embodiment, treatment cycles comprise multiple doses of daunorubicin administered to a subject in need thereof for 4 days. In one embodiment, treatment cycles comprise multiple doses of daunorubicin administered to a subject in need thereof for 5 days.

Suitable dosage amounts for the methods provided herein include, e.g., therapeutically effective amounts and prophylactically effective amounts of daunorubicin. For example, in certain embodiments, the amount of daunorubicin administered in the methods provided herein may range, e.g., between about 1 mg/m$^2$/day and about 500 mg/m$^2$/day. In certain embodiments, the amount of daunorubicin is between about 10 mg/m$^2$/day and about 300/m$^2$/day. In certain embodiments, the amount of daunorubicin is between about 20 g/m$^2$/day and about 200 g/m$^2$/day. In certain embodiments, the amount of daunorubicin is between about 30 mg/m$^2$/day and about 150 mg/m$^2$/day. In certain embodiments, the amount of daunorubicin is between about 40 mg/m$^2$/day and about 120 mg/m$^2$/day. In certain embodiments, the amount of daunorubicin is between about 50 mg/m$^2$/day and about 100 mg/m$^2$/day. In certain embodiments, the amount of a daunorubicin is between about 60 mg/m$^2$/day and about 90 mg/m$^2$/day. In certain embodiments, the amount of daunorubicin is between about 70 mg/m$^2$/day and about 80 mg/m$^2$/day.

In certain embodiments, the particular dosage of daunorubicin is about 10 mg/m$^2$/day. In one embodiment, the particular dosage is about 15 mg/m$^2$/day. In one embodiment, the particular dosage is about 20 mg/m$^2$/day. In one embodiment, the particular dosage is about 25 mg/m$^2$/day. In one embodiment, the particular dosage is about 30 mg/m$^2$/day. In one embodiment, the particular dosage is about 35 mg/m$^2$/day. In one embodiment, the particular dosage is about 40 mg/m$^2$/day. In one embodiment, the particular dosage is about 45 mg/m$^2$/day. In one embodiment, the particular dosage is about 50 mg/m$^2$/day. In one embodiment, the particular dosage is about 55 mg/m$^2$/day. In one embodiment, the particular dosage is about 60 mg/m$^2$/day. In one embodiment, the particular dosage is about 65 mg/m$^2$/day. In one embodiment, the particular dosage is about 70 mg/m$^2$/day. In one embodiment, the particular dosage is about 80 mg/m$^2$/day. In one embodiment, the particular dosage is about 90 mg/m$^2$/day. In one embodiment, the particular dosage is about 100 mg/m$^2$/day.

In certain embodiments, the particular dosage of daunorubicin is up to about 10 mg/m$^2$/day. In one embodiment, the particular dosage is up to about 15 mg/m$^2$/day. In one embodiment, the particular dosage is up to about 20 mg/m$^2$/day. In one embodiment, the particular dosage is up to about 25 mg/m$^2$/day. In one embodiment, the particular dosage is up to about 30 mg/m$^2$/day. In one embodiment, the particular dosage is up to about 35 mg/m$^2$/day. In one embodiment, the particular dosage is up to about 40 mg/m$^2$/day. In one embodiment, the particular dosage is up to about 45 mg/m$^2$/day. In one embodiment, the particular dosage is up to about 50 mg/m$^2$/day. In one embodiment, the particular dosage is up to about 55 mg/m$^2$/day. In one embodiment, the particular dosage is up to about 60 mg/m$^2$/day. In one embodiment, the particular dosage is up to about 70 mg/m$^2$/day. In one embodiment, the particular dosage is up to about 80 mg/m$^2$/day. In one embodiment, the particular dosage is up to about 90 mg/m$^2$/day. In one embodiment, the particular dosage is up to about 100 mg/m$^2$/day.

In one embodiment, depending on the disease to be treated and the subject's condition, idarubicin may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Daunorubicin may be formulated in suitable dosage unit with pharmaceutically acceptable excipients, carriers, adjuvants and vehicles, appropriate for each route of administration. In one embodiment, daunorubicin is administered intravenously.

In certain embodiments, treatment cycles comprise multiple doses of idarubicin administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of idarubicin administered to a subject in need thereof over 1 to 8 days. In one embodiment, treatment cycles comprise multiple doses of idarubicin administered to a subject in need thereof over 2 to 6 days. In one embodiment, treatment cycles comprise multiple doses of idarubicin administered to a subject in need thereof for 2 days. In one embodiment, treatment cycles comprise multiple doses of idarubicin administered to a subject in need thereof for 3 days. In one embodiment, treatment cycles comprise multiple doses of idarubicin administered to a subject in need thereof for 4 days. In one embodiment, treatment cycles comprise multiple doses of idarubicin administered to a subject in need thereof for 5 days.

Suitable dosage amounts for the methods provided herein include, e.g., therapeutically effective amounts and prophylactically effective amounts of idarubicin. For example, in certain embodiments, the amount of idarubicin administered in the methods provided herein may range, e.g., between about 0.5 mg/m$^2$/day and about 50 mg/m$^2$/day. In certain embodiments, the amount of idarubicin is between about 1 mg/m$^2$/day and about 25/m$^2$/day. In certain embodiments, the amount of idarubicin is between about 2 mg/m$^2$/day and about 20 mg/m$^2$/day. In certain embodiments, the amount of idarubicin is between about 3 mg/m$^2$/day and about 15 mg/m$^2$/day. In certain embodiments, the amount of idarubicin is between about 5 mg/m$^2$/day and about 14 mg/m$^2$/day. In certain embodiments, the amount of idarubicin is between about 10 mg/m$^2$/day and about 13 mg/m$^2$/day.

In certain embodiments, the particular dosage of idarubicin is about 1 mg/m$^2$/day. In one embodiment, the particular dosage is about 2 mg/m$^2$/day. In one embodiment, the particular dosage is about 3 mg/m$^2$/day. In one embodiment, the particular dosage is about 4 mg/m$^2$/day. In one embodiment, the particular dosage is about 5 mg/m$^2$/day. In one embodiment, the particular dosage is about 6 mg/m$^2$/day. In one embodiment, the particular dosage is about 7 mg/m$^2$/day. In one embodiment, the particular dosage is about 8 mg/m$^2$/day. In one embodiment, the particular dosage is about 9 mg/m$^2$/day. In one embodiment, the particular dosage is about 10 mg/m$^2$/day. In one embodiment, the particular dosage is about 11 mg/m$^2$/day. In one embodiment, the particular dosage is about 12 mg/m$^2$/day. In one embodiment, the particular dosage is about 13 mg/m$^2$/day. In one embodiment, the particular dosage is about 14 mg/m$^2$/day. In one embodiment, the particular dosage is about 15 mg/m$^2$/day. In one embodiment, the particular dosage is about 16 mg/m$^2$/day. In one embodiment, the particular dosage is about 17 mg/m$^2$/day. In one embodiment, the particular dosage is about 18 mg/m$^2$/day. In one embodiment, the particular dosage is about 19 mg/m$^2$/day. In one embodiment, the particular dosage is about 120 mg/m$^2$/day.

In certain embodiments, the particular dosage of idarubicin is up to about 1 mg/m$^2$/day. In one embodiment, the particular dosage is up to about 2 mg/m²/day. In one embodiment, the particular dosage is up to about 3 mg/m²/day. In one embodiment, the particular dosage is up to about 4 mg/m²/day. In one embodiment, the particular dosage is up to about 5 mg/m²/day. In one embodiment, the particular dosage is up to about 6 mg/m²/day. In one embodiment, the particular dosage is up to about 7 mg/m²/day. In one embodiment, the particular dosage is up to about 8 mg/m²/day. In one embodiment, the particular dosage is up to about 9 mg/m²/day. In one embodiment, the particular dosage is up to about 10 mg/m²/day. In one embodiment, the particular dosage is up to about 11 mg/m²/day. In one embodiment, the particular dosage is up to about 12 mg/m²/day. In one embodiment, the particular dosage is up to about 13 mg/m²/day. In one embodiment, the particular dosage is up to about 14 mg/m²/day. In one embodiment, the particular dosage is up to about 15 mg/m²/day. In one embodiment, the particular dosage is up to about 16 mg/m²/day. In one embodiment, the particular dosage is up to about 17 mg/m²/day. In one embodiment, the particular dosage is up to about 18 mg/m²/day. In one embodiment, the particular dosage is up to about 19 mg/m²/day. In one embodiment, the particular dosage is up to about 20 mg/m²/day.

In one embodiment, depending on the disease to be treated and the subject's condition, mitoxantrone may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Mitoxantrone may be formulated in suitable dosage unit with pharmaceutically acceptable excipients, carriers, adjuvants and vehicles, appropriate for each route of administration. In one embodiment, mitoxantrone is administered intravenously.

In certain embodiments, treatment cycles comprise multiple doses of mitoxantrone administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of mitoxantrone administered to a subject in need thereof over 1 to 15 days. In one embodiment, treatment cycles comprise multiple doses of mitoxantrone administered to a subject in need thereof over 2 to 10 days. In one embodiment, treatment cycles comprise multiple doses of mitoxantrone administered to a subject in need thereof for 2 days. In one embodiment, treatment cycles comprise multiple doses of mitoxantrone administered to a subject in need thereof for 3 days. In one embodiment, treatment cycles comprise multiple doses of mitoxantrone administered to a subject in need thereof for 4 days. In one embodiment, treatment cycles comprise multiple doses of mitoxantrone administered to a subject in need thereof for 5 days. In one embodiment, treatment cycles comprise multiple doses of mitoxantrone administered to a subject in need thereof for 6 days. In one embodiment, treatment cycles comprise multiple doses of mitoxantrone administered to a subject in need thereof for 7 days. In one embodiment, treatment cycles comprise multiple doses of mitoxantrone administered to a subject in need thereof for 8 days.

Suitable dosage amounts for the methods provided herein include, e.g., therapeutically effective amounts and prophylactically effective amounts of mitoxantrone. For example, in certain embodiments, the amount of mitoxantrone administered in the methods provided herein may range, e.g., between about 0.5 mg/m²/day and about 50 mg/m²/day. In certain embodiments, the amount of mitoxantrone is between about 1 mg/m²/day and about 25/m²/day. In certain embodiments, the amount of mitoxantrone is between about 5 mg/m²/day and about 20 mg/m²/day. In certain embodiments, the amount of mitoxantrone is between about 10 mg/m²/day and about 15 mg/m²/day.

In certain embodiments, the particular dosage of mitoxantrone is about 1 mg/m²/day. In one embodiment, the particular dosage is about 2 mg/m²/day. In one embodiment, the particular dosage is about 3 mg/m²/day. In one embodiment, the particular dosage is about 4 mg/m²/day. In one embodiment, the particular dosage is about 5 mg/m²/day. In one embodiment, the particular dosage is about 6 mg/m²/day. In one embodiment, the particular dosage is about 7 mg/m²/day. In one embodiment, the particular dosage is about 8 mg/m²/day. In one embodiment, the particular dosage is about 9 mg/m²/day. In one embodiment, the particular dosage is about 10 mg/m²/day. In one embodiment, the particular dosage is about 11 mg/m²/day. In one embodiment, the particular dosage is about 12 mg/m²/day. In one embodiment, the particular dosage is about 13 mg/m²/day. In one embodiment, the particular dosage is about 14 mg/m²/day. In one embodiment, the particular dosage is about 15 mg/m²/day. In one embodiment, the particular dosage is about 16 mg/m²/day. In one embodiment, the particular dosage is about 17 mg/m²/day. In one embodiment, the particular dosage is about 18 mg/m²/day. In one embodiment, the particular dosage is about 19 mg/m²/day. In one embodiment, the particular dosage is about 20 mg/m²/day.

In certain embodiments, the particular dosage of mitoxantrone is up to about 1 mg/m²/day. In one embodiment, the particular dosage is up to about 2 mg/m²/day. In one embodiment, the particular dosage is up to about 3 mg/m²/day. In one embodiment, the particular dosage is up to about 4 mg/m²/day. In one embodiment, the particular dosage is up to about 5 mg/m²/day. In one embodiment, the particular dosage is up to about 6 mg/m²/day. In one embodiment, the particular dosage is up to about 7 mg/m²/day. In one embodiment, the particular dosage is up to about 8 mg/m²/day. In one embodiment, the particular dosage is up to about 9 mg/m²/day. In one embodiment, the particular dosage is up to about 10 mg/m²/day. In one embodiment, the particular dosage is up to about 11 mg/m²/day. In one embodiment, the particular dosage is up to about 12 mg/m²/day. In one embodiment, the particular dosage is up to about 13 mg/m²/day. In one embodiment, the particular dosage is up to about 14 mg/m²/day. In one embodiment, the particular dosage is up to about 15 mg/m²/day. In one embodiment, the particular dosage is up to about 16 mg/m²/day. In one embodiment, the particular dosage is up to about 17 mg/m²/day. In one embodiment, the particular dosage is up to about 18 mg/m²/day. In one embodiment, the particular dosage is up to about 19 mg/m²/day. In one embodiment, the particular dosage is up to about 20 mg/m²/day.

In one embodiment, depending on the disease to be treated and the subject's condition, etoposide may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Etoposide may be formulated in suitable dosage unit with pharmaceutically acceptable excipients, carriers, adjuvants and vehicles, appropriate for each route of administration. In one embodiment, etoposide is administered intravenously. In one embodiment, etoposide is administered orally.

In certain embodiments, treatment cycles comprise multiple doses of etoposide administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of etoposide administered to a subject in need thereof over 1 to 15 days. In one embodiment, treatment cycles comprise multiple doses of etoposide administered to a subject in need thereof over 2 to 10 days. In one embodiment, treatment cycles comprise multiple doses of etoposide administered to a subject in need thereof for 2 days. In one embodiment, treatment cycles comprise multiple doses of etoposide administered to a subject in need thereof for 3 days. In one embodiment, treatment cycles comprise multiple doses of mitoxantrone administered to a subject in need thereof for 4 days. In one embodiment, treatment cycles comprise multiple doses of mitoxantrone administered to a subject in need thereof for 5 days. In one embodiment, treatment cycles comprise multiple doses of mitoxantrone administered to a subject in need thereof for 6 days. In one embodiment, treatment cycles comprise multiple doses of mitoxantrone administered to a subject in need thereof for 7 days. In one embodiment, treatment cycles comprise multiple doses of mitoxantrone administered to a subject in need thereof for 8 days.

Suitable dosage amounts for the methods provided herein include, e.g., therapeutically effective amounts and prophylactically effective amounts of etoposide. For example, in certain embodiments, the amount of etoposide administered in the methods provided herein may range, e.g., between about 10 mg/m$^2$/day and about 1000 mg/m$^2$/day. In certain embodiments, the amount of etoposide is between about 50 mg/m$^2$/day and about 500/m$^2$/day. In certain embodiments, the amount of etoposide is between about 75 mg/m$^2$/day and about 250 mg/m$^2$/day. In certain embodiments, the amount of etoposide is between about 100 mg/m$^2$/day and about 200 mg/m$^2$/day.

In certain embodiments, the particular dosage of etoposide is about 10 mg/m$^2$/day. In one embodiment, the particular dosage is about 25 mg/m$^2$/day. In one embodiment, the particular dosage is about 50 mg/m$^2$/day. In one embodiment, the particular dosage is about 75 mg/m$^2$/day. In one embodiment, the particular dosage is about 100 mg/m$^2$/day. In one embodiment, the particular dosage is about 125 mg/m$^2$/day. In one embodiment, the particular dosage is about 150 mg/m$^2$/day. In one embodiment, the particular dosage is about 175 mg/m$^2$/day. In one embodiment, the particular dosage is about 200 mg/m$^2$/day.

In certain embodiments, the particular dosage of etoposide is up to about 10 mg/m$^2$/day. In one embodiment, the particular dosage is up to about 25 mg/m$^2$/day. In one embodiment, the particular dosage is up to about 50 mg/m$^2$/day. In one embodiment, the particular dosage is up to about 75 mg/m$^2$/day. In one embodiment, the particular dosage is up to about 100 mg/m$^2$/day. In one embodiment, the particular dosage is up to about 125 mg/m$^2$/day. In one embodiment, the particular dosage is up to about 150 mg/m$^2$/day. In one embodiment, the particular dosage is up to about 175 mg/m$^2$/day. In one embodiment, the particular dosage is up to about 200 mg/m$^2$/day.

In one embodiment, a method provided herein comprises administering the COMPOUND 1 and the induction therapy in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, a method provided herein comprises administering the COMPOUND 1 and the consolidation therapy in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, COMPOUND 2 is administered orally once a day. In one embodiment, COMPOUND 2 is administered on days 1-28 of each 28-day cycle. In one embodiment, 50 mg of COMPOUND 2 is administered orally once a day. In another embodiment, 100 mg of COMPOUND 2 is administered orally once a day. In yet another embodiment, 200 mg of COMPOUND 2 is administered orally once a day.

In one embodiment, the induction therapy comprises cytarabine administered for 7 days and daunorubicin administered for 3 days. In one embodiment, the induction therapy comprises cytarabine administered for 7 days and idarubicin administered for 3 days.

In one embodiment, in the methods provided herein, the induction cycle may be repeated no later than 35 days from the previous induction cycle. In one embodiment, in the methods provided herein, the induction cycle may be repeated not earlier than 14 days after bone marrow aspirate/biopsy. In one embodiment, in the methods provided herein, the induction cycle may be repeated by administering cytarabine for 5 days and daunorubicin or idarubicin for 2 days starting no later than 35 days from the previous induction cycle. In one embodiment, in the methods provided herein, the induction cycle may be repeated by administering cytarabine for 5 days and daunorubicin or idarubicin for 2 days starting not earlier than 14 days after bone marrow aspirate/biopsy.

In one embodiment, the consolidation therapy comprises cytarabine administered for 3 days. In one embodiment, the consolidation therapy comprises cytarabine administered on days 1, 3, and 5 of the cycle. In one embodiment, the consolidation therapy comprises mitoxantrone and etoposide administered for 5 days. In one embodiment, in the methods provided herein, the consolidation cycle can be performed within 28-42.

EXAMPLES

Example 1. Phase a Phase 1, Multicenter, Open-Label, Safety Study of COMPOUND 1 and COMPOUND 2 in Combination with Induction Therapy and Consolidation Therapy in Patients with Newly Diagnosed Acute Myeloid Leukemia with an IDH1 and/or IDH2 Mutation Objectives
Primary Objective:
Determine the safety and tolerability of 2-methyl-[(4-[6-(trifluoromethyl)pyridin-2-yl]-6-{[2-(trifluoromethyl)pyridin-4-yl]amino}-1,3,5-triazin-2-yl)amino]propan-2-ol (hereinafter COMPOUND 1) and COMPOUND 2 when administered with induction and consolidation therapy in patients with newly diagnosed acute myeloid leukemia (AML) with isocitrate dehydrogenase-1 (IDH1) and/or isocitrate dehydrogenase-2 (IDH2) mutation.

Secondary Objectives:
characterize the pharmacokinetics (PK) of COMPOUND 1 and COMPOUND 2 in plasma samples when administered with AML induction therapy and consolidation therapy;
establish the recommended Phase 2 dose (RP2D) of COMPOUND 1 and COMPOUND 2 when administered with AML induction and consolidation therapy;
evaluate the 2-hydroxygluturate (2-HG) levels in plasma;
evaluate the clinical activity of COMPOUND 1 in combination with AML induction and consolidation therapy.
Study Outcome Measures
Safety Outcome Measures
Safety will be evaluated by:
dose-limiting toxicities (DLTs);
adverse events (AEs), serious adverse events (SAEs), and AEs leading to discontinuation;
safety laboratory test results, physical examination, vital signs, 12-lead electrocardiograms (ECGs), left ventricular ejection fraction (LVEF), and Eastern Cooperative Oncology Group (ECOG) performance status (PS);
drug exposure, including dose intensities and dose modifications.
Pharmacokinetic and Pharmacodynamic Outcome Measures
The PK and PD profile of COMPOUND 1 and COMPOUND 2 and will be evaluated by:
plasma concentrations and PK parameters of COMPOUND 1 and COMPOUND 2 and the major metabolite of COMPOUND 1;
plasma concentrations of 2-HG in relation to plasma concentrations of COMPOUND 1 and COMPOUND 2 over time.
Clinical Activity Outcome Measures
The clinical activity of COMPOUND 1 and COMPOUND 2 in combination with AML induction and consolidation therapy will be evaluated by:
complete remission rate (CRR);
objective response rate (ORR), including complete remission (CR), CR with incomplete hematologic recovery—neutrophil and/or platelet (CRi [includes CR with incomplete platelet recovery (CRp)]), partial remission (PR), and morphologic leukemia-free state (MLFS);
duration of response (DOR) and duration of CR (DOCR);
time to response (TTR) and time to CR (TTCR);
event-free survival (EFS);
overall survival (OS).
Study Design
COMPOUND 1 and COMPOUND 2 is an open-label, multicenter, Phase 1 clinical trial to evaluate the safety of COMPOUND 1 and COMPOUND 2 in combination with AML induction and consolidation therapy. The study will evaluate 1 dose level of COMPOUND 2 in patients with an IDH1 mutation and 2 dose levels of COMPOUND 1 in patients with an IDH2 mutation. COMPOUND 1 or COMPOUND 2 will be administered with 2 types of AML induction therapies (cytarabine with either daunorubicin or idarubicin) and 2 types of AML consolidation therapies (mitoxantrone with etoposide [ME] or cytarabine). For patients who have a dual IDH1 and IDH2 mutation, assignment to COMPOUND 1 or COMPOUND 2 will be based on Investigator and Medical Monitor decision.
Patients will be treated as follows:
all patients will receive induction therapy (7+3 cytarabine, daunorubicin/idarubicin) in combination with COMPOUND 1 or COMPOUND 2;
after 1 cycle of induction therapy, patients may undergo a second induction cycle given as per institutional practice (i.e., repeat 7+3, or 7+3 at attenuated doses or schedule such as 5+2 cytarabine, daunorubicin/idarubicin). The second induction cycle may be started after the Day 14 bone marrow aspirate/biopsy (if performed) and no later than 35 days following Day 1 of the first induction;

patients who do not achieve CR or CRi (including CRp) after a maximum of 2 inductions will be discontinued from the study;

patients who achieve CR or CRi (including CRp) at the end of induction therapy will go on to receive consolidation therapy (ME or up to 4 cycles of intermediate-dose cytarabine) in combination with COMPOUND 1 or COMPOUND 2. Consolidation treatment should begin within approximately 2 weeks after hematologic recovery in the last induction cycle, or no later than 12 weeks after Day 1 of the first induction cycle;

patients who complete consolidation therapy and are in CR or CRi (including CRp) may continue on maintenance therapy and receive daily treatment with COMPOUND 1 or COMPOUND 2 for up to 1 year from Day 1 of the first induction cycle, or until relapse, development of an unacceptable toxicity, or hematopoietic stem cell transplant (HSCT) based on Investigator and Medical Monitor decision.

Response will be evaluated by the Investigator based on International Working Group (IWG) criteria.

The type of induction therapy and/or consolidation therapy each patient receives will be based on Investigator discretion and/or open cohorts.

The enrollment into each type of induction therapy will be done in parallel for the first cohort of 6 DLT evaluable patients for daunorubicin with cytarabine and idarubicin with cytarabine for COMPOUND 1 and COMPOUND 2 groups. For consolidation therapy, a minimum of 6 evaluable patients each will receive either cytarabine 1-1.5 g/m$^2$ or ME. Patients with favorable risk cytogenetics may receive 2-3 g/m$^2$ cytarabine; there is no minimum number of patients required for this group.

Definition of Dose-Limiting Toxicity

Dose-limiting toxicity is defined as any of the following AEs that are clinically significant and considered by the Investigator to be related to COMPOUND 1 or COMPOUND 2 as the single contributor or in combination with daunorubicin, idarubicin, or cytarabine.

Hematologic:

Prolonged myelosuppression, with Grade 4 neutropenia or thrombocytopenia lasting≥42 days from Day 1 of the first induction cycle in the absence of persistent leukemia (by National Cancer Institute Common Terminology Criteria for Adverse Events [NCI CTCAE], version 4.03, leukemia-specific criteria, i.e., marrow cellularity<5% on Day 28 or later from the start of study drug without evidence of leukemia). Leukemia-specific grading should be used for cytopenias (based on percentage decrease from baseline: 50 to 75%=Grade 3, >75%=Grade 4).

Non Hematologic:

All toxicity≥Grade 3 not due to underlying AML or complications of the disease or myelosuppressive treatment, with the exception of ≥Grade 3 blood bilirubin increases in subjects with a UGT1A1 mutation receiving COMPOUND 1. Since isolated blood bilirubin increases have been seen in subjects with a UGT1A1 mutation receiving COMPOUND 1, blood bilirubin increases of >5×upper limit of normal (ULN) may be considered a DLT in these subjects.

The definition of a DLT does not include the expected systemic and infectious complications of treatment with anthracyclines and cytarabine, including, but not limited to:

anorexia requiring total parenteral nutrition;

fatigue necessitating bed rest;

gastrointestinal infectious complications such as colitis, typhilitis, mucositis, stomatitis;

liver function test (LFT) elevations, metabolic or electrolyte laboratory abnormality that return to baseline within 14 days.

The Clinical Study Team, including representatives from the Sponsor, Medical Monitor, and participating Investigators, also will review any emergent toxicity that is not explicitly defined by the DLT criteria to determine if any warrant a DLT designation.

Toxicity severity will be graded according to the NCI CTCAE version 4.03. All AEs that cannot clearly be determined to be unrelated to COMPOUND 1 or COMPOUND 2 will be considered relevant to determining DLTs and will be reviewed by the Clinical Study Team.

DLT-Evaluable Patients

DLT-evaluable patients for induction therapy are defined as those patients who receive all doses of the first cycle of induction chemotherapy and at least 75% of COMPOUND 1 or COMPOUND 2 doses in the first 28 days from first dose of induction therapy, or experience a DLT during the first 28 days. In addition, patients must take all 3 COMPOUND 1 or COMPOUND 2 doses on Days 1 to 3 and at least 2 COMPOUND 1 or COMPOUND 2 doses on Days 4 to 7 of first induction to be considered DLT-evaluable. A patient diary will be used during outpatient treatment to record details around COMPOUND 1 and COMPOUND 2 dosing.

Safety Evaluation for Induction Therapy

This study will use a "6+6" design for COMPOUND 1 and COMPOUND 2 dose determination, which is similar to the standard "3+3" design but with more accuracy of identifying the RP2D as more patients are evaluated at each dose level. Each dose cohort will plan to enroll 6 DLT-evaluable patients, starting with Dose Level 1. Dose escalation or de-escalation decisions will be made independently for each type of induction combination therapy (i.e., cytarabine with either daunorubicin or idarubicin. For COMPOUND 2, there is only 1 dose de-escalation allowed to dose Level −1. For COMPOUND 1, there is 1 dose escalation allowed to Dose Level 2 and 1 dose de-escalation allowed to Dose Level −1.

Guidelines for COMPOUND 1 Dose Evaluation:

If 0 or 1 of 6 patients experiences a DLT at the current dose level, that dose will be declared safe for that induction regimen. If at Dose Level 1, dose escalation will proceed to Level 2 if Level 1 is determined also to be safe in consolidation (see below). Approximately 6 additional patients will then be enrolled at Dose Level 1 as needed for evaluation of consolidation at this dose and further evaluation of safety.

If 2 of 6 patients experience a DLT, the cohort will be expanded with 6 additional patients for a total of 12 patients at this dose level.

If 3 or fewer of 12 patients experience a DLT, the current dose level will be declared safe for induction. If at Dose Level 1, dose escalation will proceed to Level 2 if Level 1 is determined also to be safe in consolidation.

If 4 or more of 12 patients experience a DLT at Dose Level 1: Dose de-escalation will proceed to Dose Level −1. If 4 or more of 12 patients experience a DLT at Dose Level 2: Return to Dose Level 1. If 4 or more of 12 patients experience a DLT at Dose Level −1: That induction regimen will be closed to further enrollment.

If 3 or more of 6 patients experience a DLT at Dose Level 1: Dose de-escalation will proceed to Dose Level −1. If 3 or more of 6 patients experience a DLT at Dose Level 2: Return to Dose Level 1. If 3 or more of 6 patients experience a DLT at Dose Level −1: hat induction regimen will be closed to further enrollment.

Guidelines for COMPOUND 2 Dose Evaluation:

No dose escalation for Compound 2.

If 0 or 1 of 6 patients experiences a DLT at Dose Level 1, that dose level will be declared safe for that induction regimen. Approximately 6 additional patients will be enrolled at this dose level as needed for evaluation of consolidation at this dose and further evaluation of safety.

If 2 of 6 patients experience a DLT at Dose Level 1, the cohort will be expanded with 6 additional patients for a total of 12 patients at this dose level.

If 3 or fewer of 12 patients experience a DLT, Dose Level 1 will be declared safe for induction.

If 4 or more of 12 patients experience a DLT, dose de-escalation will proceed to Dose Level −1.

If 3 or more of 6 patients experience a DLT, dose de-escalation will proceed to Dose Level −1.

If the dose is de-escalated to Dose Level −1, the evaluation of that dose will occur as described above. If 3 or more of 6 patients experience or 4 or more of 12 patients experience a DLT at Dose Level −1, that induction regimen will be closed to further enrollment.

Safety Evaluation for Consolidation Therapy

The safety of consolidation therapy at each dose level will be reviewed regularly and evaluated when 6 patients have completed at least 28 days of consolidation treatment or have discontinued due to toxicity. All available safety data will be evaluated to determine if the dose is safe and tolerable.

For COMPOUND 1, the dose escalation to 200 mg requires that 100 mg is determined safe for both induction (either daunorubicin with cytarabine or idarubicin with cytarabine) and consolidation (either cytarabine 1-1.5 g/m$^2$ or ME). The daunorubicin+cytarabine+COMPOUND 1 200 mg induction cohort will open if daunorubicin+cytarabine+COMPOUND 1 100 mg is deemed safe and the idarubicin+cytarabine+COMPOUND 1 200 mg induction cohort will open if idarubicin+cytarabine+COMPOUND 1 100 mg is deemed safe. The cytarabine 1-1.5 g/m$^2$ (and cytarabine 2-3 g/m$^2$)+COMPOUND 1 200 mg consolidation cohort will open if cytarabine 1-1.5 g/m$^2$ (or cytarabine 2-3 g/m$^2$)+COMPOUND 1 100 mg is deemed safe and the ME+COMPOUND 1 200 mg consolidation cohort will open if ME+COMPOUND 1 100 mg is deemed safe.

Interim Safety Review

Interim safety reviews will be conducted following completion of each induction dosing cohort (i.e., all cohort patients have completed their DLT windows) and when the first 6 evaluable consolidation patients have completed at least 28 days of treatment or have discontinued due to toxicity.

Safety assessments include the following:
observed toxicity including DLTs;
review of AEs/SAEs;
PK/PD data;
review of cardiac and laboratory data;
bone marrow aspirate/biopsy.

The safety assessment will be made by the Clinical Study Team. Dose reduction of COMPOUND 1 or COMPOUND 2 may be made earlier for patient safety or at the discretion of the Investigator in discussion with the Sponsor.

Study Drug

A single dose of COMPOUND 1 or COMPOUND 2 will be administered orally starting on Day 1 of induction prior to daunorubicin/idarubicin and cytarabine and will be administered daily through treatment discontinuation or end of study. Doses of COMPOUND 1 or COMPOUND 2 must be taken within ±4 hours of the scheduled dose at approximately the same time each day. Each COMPOUND 1 daily dose should be taken 2 hours after fasting (water is allowed), and food intake should be avoided for at least 1 hour after administration of COMPOUND 1. All patients are advised to avoid grapefruit and grapefruit products.

The dose of COMPOUND 2 administered to patients with an IDH1 mutation will be 500 mg (unless there is a dose reduction to 250 mg due to DLTs. The dose of COMPOUND 1 administered to patients with an IDH2 mutation will be dependent upon which dose cohort is open for enrollment when the patient qualifies for the study. Dose levels are provided in 7. No intra-patient dose escalation will be permitted during induction or consolidation therapy for COMPOUND 1.

Patients who continue onto maintenance therapy following consolidation may receive daily COMPOUND 1 or COMPOUND 2 for up to 1 year from Day 1 of the first induction cycle. Patients receiving COMPOUND 2 will continue on treatment at their current dose. Patients receiving COMPOUND 1 100 mg may continue on treatment at their current dose or may have a dose escalation to 200 mg if that dose has been established as safe in induction and consolidation. Intra-patient dose escalation to 200 mg during maintenance with COMPOUND 1 should be confirmed with the Medical Monitor.

Alternative dosing schedules for COMPOUND 1 or COMPOUND 2, including administration of the same total daily dose using different schedules in concurrent cohorts, may be explored as agreed upon by the Clinical Study Team.

TABLE 7

Dose Levels for COMPOUND 1
COMPOUND 1 (IDH2 Mutation)

| Dose Level | Dose |
|---|---|
| −1 | 50 mg |
| 1 | 100 mg |
| 2 | 200 mg |

TABLE 8

Dose Levels for COMPOUND 2
COMPOUND 2 (IDH1 Mutation)

| Dose Level | Dose |
|---|---|
| −1 | 250 mg |
| 1 | 500 mg |

TABLE 9

Induction Schedule with COMPOUND 1 or COMPOUND 2

| Treatment | Day 1 | Day 2 | Day 3 | Days 4-7 | Days 8-28[a,b] |
|---|---|---|---|---|---|
| IV cytarabine 200 mg/m$^2$ [c] | X | X | X | X | |
| IV daunorubicin 60 mg/m$^2$; or IV idarubicin 12 mg/m$^2$ [c] | X | X | X | | |

TABLE 9-continued

Induction Schedule with COMPOUND 1 or COMPOUND 2

| Treatment | Day 1 | Day 2 | Day 3 | Days 4-7 | Days 8-28[a,b] |
|---|---|---|---|---|---|
| Oral COMPOUND 1 or COMPOUND 2 | X | X | X | X | X |

[a]Patients may undergo a second induction cycle as per institutional practive (i.e., repeat 7 + 3, or 7 + 3 at attenuated doses or schedule such as 5 + 2 cytarabine, daunorubicin/ idarubicin) starting after the Day 14 bone marrow aspirate/biopsy (if performed) and no later than 35 days following Day 1 of the first induction.
[b]Patients should take COMPOUND 1 or COMPOUND 2 on all days of the induction cycle(s) (i.e., through last day of cycle if induction cycle is longer than 28 days).
[c] Dose adjustments may be made to cytarabine, daunorubicin, and/or idarubicin as indicated by the prescribing information.

TABLE 10

Consolidation Schedule with COMPOUND 1 or COMPOUND 2

| Treatment | Day 1 | Day 2 | Day 3 | Day 4 | Day 5 | Days 6-28[a] |
|---|---|---|---|---|---|---|
| IV cytarabine[b]; or mitoxantrone 10 mg/m$^2$ and etoposide 100 mg/m$^2$ [c,d] | X | X | X | X | X | |
| Oral COMPOUND 1 or COMPOUND 2 | X | X | X | X | X | X |

[a]A window of 28 to 42 days is allowed for each consolidation cycle. Patients should take Compound 1 or Compound 2 on all days of the consolidation cycle(s) (i.e., through last day of cycle if consolidation cycle is longer than 28 days).
[b]cytarabine will be given at or between doses of 1 g/m$^2$ and 1.5 g/m$^2$ IV q12h, Days 1-3. Patients with favorable risk cytogenetics can receive higher doses of cytarabine at or between doses of 2-3 g/m$^2$ IV q12h, Days 1-3 or Days 1, 3, and 5. Patients may receive up to 4 consolidation cycles with cytarabine.
[c]Mitoxantrone 10 mg/m$^2$ and etoposide 100 mg/m$^2$ may be chosen as consolidation regimen as per institutional practice.
[d]Dose adjustments may be made to cytarabine, mitoxantrone and/or etoposide as indicated by the prescribing information.

Estimated Number of Patients

A total of approximately 72 DLT evaluable patients (approximately 12 patients required at each dose level of COMPOUND 1 or COMPOUND 2 per each type of 7+3 induction therapy) will be enrolled in this study. Taking into account an up to 20% drop out during the DLT evaluation period, this study will enroll up to a total of approximately 90 patients. Additional patients may be enrolled in a dose level to replace patients who are not evaluable for DLT, fill consolidation cohorts, or for further exploring safety, PK, PK/PD, or preliminary clinical activity.

Inclusion Criteria

Patients are eligible for inclusion in the study if they meet the following criteria: ≥18 years of age;

previously untreated AML (de novo or secondary) defined according to WHO criteria, excluding APL [AML with t(15;17)], with locally documented IDH1 and/or IDH2 gene mutation scheduled for induction therapy followed by consolidation therapy. Secondary AML is defined as AML arising after myelodysplastic syndromes (MDS) or antecedent hematologic disorder (AHD) or AML arising after exposure to genotoxic injury including radiation and/or chemotherapy. Patients may have had previous treatment with hypomethylating agents (HMAs) for MDS;

ECOG PS of 0 to 2;

Adequate hepatic function as evidenced by:

serum total bilirubin≤1.5×ULN unless considered due to Gilbert's disease, a gene mutation in UGT1A1 (only for patients who will be receiving COMPOUND 1), or leukemic involvement following approval by the Medical Monitor;

aspartate aminotransferase (AST), alanine aminotransferase (ALT), and alkaline phosphatase (ALP)≤3.0×ULN, unless considered due to leukemic involvement following approval by the Medical Monitor;

adequate renal function as evidenced by serum creatinine≤2.0×ULN or creatinine clearance>40 mL/min based on the Cockroft-Gault glomerular filtration rate (GFR);

agree to serial blood and bone marrow sampling;

meet any criteria necessary for the safe and proper use of the induction and consolidation agents involved in this trial;

able to understand and willing to sign an informed consent form. A legally authorized representative may consent on behalf of a subject who is otherwise unable to provide informed consent, if acceptable to, and approved by, the site's Institutional Review Board (IRB)/Independent Ethics Committee (IEC);

female subjects with reproductive potential must agree to undergo a medically supervised pregnancy test prior to starting study drug. The first pregnancy test will be performed at screening (within 7 days prior to first study drug administration). A pregnancy test should also be performed on the day of the first study drug administration and confirmed negative prior to dosing as well as before dosing on Day 1 of all subsequent cycles;

female subjects with reproductive potential must have a negative serum pregnancy test within 7 days prior to the start of the therapy. Subjects with reproductive potential are defined as sexually mature women who have not undergone a hysterectomy, bilateral oophorectomy or tubal occlusion or who have not been naturally postmenopausal for at least 24 consecutive months. Females of reproductive potential as well as fertile men and their partners who are female of reproductive potential must agree to abstain from sexual intercourse or to use two highly effective forms of contraception from the time of giving informed consent, during the study, and for 90 days (females and males) following the last dose of COMPOUND 1 or COMPOUND 2. A highly effective form of contraception is defined as hormonal oral contraceptives, injectables, patches, intrauterine devices, double-barrier method (e.g., synthetic condoms, diaphragm or cervical cap with spermicidal foam, cream, or gel) or male partner sterilization.

Exclusion Criteria

Patients are excluded from the study if they meet any of the following criteria:

prior chemotherapy for AML. Hydroxyurea is allowed for the control of peripheral leukemic blasts in subjects with leukocytosis (white blood cell [WBC] counts>30,000 µL);

taking medications with narrow therapeutic windows, unless they can be transferred to other medications prior to enrolling or unless the medications can be properly monitored during the study;

taking known strong cytochrome P450 (CYP) 3A4 inducers or inhibitors;

taking P-glycoprotein (P-gp) or breast cancer resistance protein (BCRP) transporter-sensitive substrate medications unless they can be transferred to other medications within ≥5 half-lives prior to administration of COMPOUND 1 or COMPOUND 2, or unless the medications can be properly monitored during the study;

pregnant or breast feeding;

uncontrolled active infection or uncontrolled invasive fungal infection (positive blood or tissue culture). An infection controlled with an approved or closely monitored antibiotic/antifungal treatment is allowed;

Prior history of malignancy, other than MDS or AML, unless the subject has been free of the disease for ≥1 year prior to the start of study treatment. However, subjects with the following history/concurrent conditions are allowed:

basal or squamous cell carcinoma of the skin;
carcinoma in situ of the cervix;
carcinoma in situ of the breast;
incidental histologic finding of prostate cancer;

significant active cardiac disease within 6 months prior to the start of study treatment, including New York Heart Association (NYHA) Class III or IV congestive heart failure; myocardial infarction, unstable angina and/or stroke; or LVEF<40% by echocardiogram (ECHO) or multi-gated acquisition (MUGA) scan obtained within 28 days prior to the start of study treatment;

QTc interval using Fridericia's formula (QTcF)≥450 msec or other factors that increase the risk of QT prolongation or arrhythmic events (e.g., heart failure, hypokalemia, family history of long QT interval syndrome). Bundle branch block and prolonged QTc interval are permitted with approval of the Medical Monitor;

taking medications that are known to prolong the QT interval unless they can be transferred to other medications within ≥5 half-lives prior to dosing (If equivalent medication is not available QTc will be closely monitored);

known infection with human immunodeficiency virus (HIV) or active hepatitis B or C;

dysphagia, short-gut syndrome, gastroparesis, or other conditions that limit the ingestion or gastrointestinal absorption of orally administered drugs;

clinical symptoms suggestive of active central nervous system (CNS) leukemia or known CNS leukemia. Evaluation of cerebrospinal fluid (CSF) during screening is only required if there is a clinical suspicion of CNS involvement by leukemia during screening;

immediate life-threatening, severe complications of leukemia such as uncontrolled bleeding, pneumonia with hypoxia or shock, and/or disseminated intravascular coagulation any other medical or psychological condition deemed by the Investigator to be likely to interfere with a patient's ability to give informed consent or participate in the study.

Duration of Treatment and End of Study

Duration of Treatment

Daily treatment with COMPOUND 1 or COMPOUND 2 will begin on the first day of induction therapy. All patients will receive 1 cycle of induction therapy. A second cycle of induction is permitted for patients according to the Investigator's discretion. After induction therapy, patients who achieve CR or CRi (including CRp) will receive consolidation therapy.

Patients achieving a CR or CRi (including CRp) who receive both induction and consolidation therapy, may continue to receive single agent COMPOUND 1 or COMPOUND 2 after consolidation therapy until relapse, development of an unacceptable toxicity, or HSCT, for up to 1 year from Day 1 of the first induction cycle.

HSCT

Subjects who achieve an adequate response and are eligible to have HSCT may proceed to HSCT after discontinuation of COMPOUND 1 or COMPOUND 2. Patients who have HSCT will be discontinued from the study and will be followed for survival.

Survival Follow-Up

After patients discontinue study treatment, they will be contacted approximately every 3 months to collect survival data for up to 1 year from the time of last patient enrolled.

End of Study

End of study (last patient last visit) is defined as the time at which all patients have either completed the 1-year survival follow-up or have died, discontinued the study, are lost to follow up, or withdrew consent prior completing the 1-year follow-up period.

Statistical Methods

Statistical analyses will be primarily descriptive. Study data will be summarized for disposition, demographic and baseline characteristics, safety, PK, PD, and clinical activity parameters. Categorical data will be summarized by frequency distributions (number and percentages of patients) and continuous data will be summarized by descriptive statistics (mean, standard deviation, median, minimum, and maximum). All data will be presented in by-patient listings. All summaries, listings, figures, and analyses will be performed by dose level/schedule.

The study data will be analyzed and reported in the primary clinical study report (CSR) based on all patients' data up to the time when all patients have completed induction therapy and consolidation therapy, if applicable, or discontinued the study treatment. Any additional data for patients continuing to receive study treatment or in follow up for survival past the data cutoff date for the primary CSR will be reported once all patients have discontinued the study.

Safety will be evaluated by the incidence of AEs, severity and type of AEs, and by the patient's vital signs, ECOG performance scores, clinical laboratory results, ECG, and LVEF data, drug exposure and modifications. Safety will be summarized using descriptive statistics by dose level/schedule and total.

Descriptive statistics will be used to summarize PK parameters for each dose level and, where appropriate, for the entire population. The relationships between dose and both maximum concentration ($C_{max}$) and area under the concentration time curve (AUC) will be explored graphically for dose-proportionality.

Descriptive statistics will be used to summarize PD parameters of 2-HG inhibition for each dose cohort and, where appropriate, for the entire population. The PK/PD relationship of COMPOUND 1 or COMPOUND 2 and 2-HG inhibition will be evaluated.

Response to treatment will be assessed by the site Investigators using the IWG criteria for AML. Objective response is defined as including all responses of CR, CRi (includes CRp), PR, and MLFS. Responses at each time point and best response will be listed by patient; best overall response rate and ORR will be summarized and two-sided 95% confidence intervals (CIs) on the response rates will be calculated. Time to response/remission will also be listed and summarized if appropriate.

Time-to-event outcomes, including DOR, EFS, and OS will be assessed using Kaplan-Meier methods, if appropriate. Median, 3-month, 6-month, and 1-year estimates with associated 95% CIs will be produced if appropriate.

In certain embodiments, AML patients treated with COMPOUND 1 and AML induction and consolidation therapy, for example undergoing the clinical protocol provided herein, will show a treatment response. In some embodiments, the treatment response is a Complete Response (CR), a Morphologic Leukemia-free State (MLFS), a Morphologic Complete Remission with Incomplete Neutrophil Recovery (CRi), Morphologic Complete Remission with Incomplete Platelet Recovery (CRp), or a Partial Remission (PR), according to modified IWG AML response criteria (Cheson, et al. *J Clin Oncol* 2003; 21(24):4642-9). In some embodiments, the treatment response is a hematologic improvement. In certain embodiments, AML patients treated with COMPOUND 1 and AML induction and consolidation therapy in the methods provide herein will show an improvement in event-free survival (EFS), duration of response (DOR), time to response (TTR), and/or overall survival (OS).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only

The invention claimed is:

1. A method of treating acute myelogenous leukemia (AML) characterized by the presence of a mutant allele of IDH1, comprising administering to a subject in need thereof a therapeutically effective amount of an isocitrate dehydrogenase 1 (IDH1) inhibitor and;
   a) an induction therapy regimen consisting of cytarabine and an anthracycline selected from daunorubicin and idarubicin; and
   b) a consolidation therapy regimen consisting of cytarabine;
   wherein the mutant IDH1 inhibitor is (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

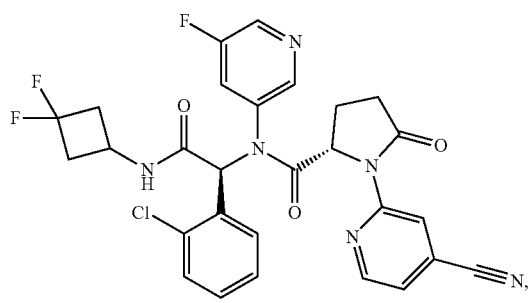 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt thereof (COMPOUND 2), and is administered during both the induction and the consolidation regimens and wherein the mutant allele of IDH1 has a mutation selected from R132H, R132C, R132L, R132V, R132S and R132GF.

2. The method of claim 1, wherein the dose of cytarabine used as an induction therapy is between about 100 $mg/m^2$/day and about 500 $mg/m^2$/day.

3. The method of claim 2, wherein the dose of cytarabine is between about 150 $mg/m^2$/day and about 300 $mg/m^2$/day.

4. The method of claim 3, wherein the dose of cytarabine is about 200 $mg/m^2$/day.

5. The method of claim 1, wherein the dose of cytarabine used as a consolidation therapy is between about 1 $g/m^2$/day and about 10 $g/m^2$/day.

6. The method of claim 5, wherein the dose of cytarabine is between about 1 $g/m^2$/day and about 5 $g/m^2$/day.

7. The method of claim 6, wherein the dose of cytarabine is 1 $g/m^2$/day, or 1.5 $g/m^2$/day, or 2 $g/m^2$/day, or 3 $g/m^2$/day.

8. The method of claim 1, wherein the anthracycline is daunorubicin administered at a dose between about 10 $mg/m^2$/day and about 300 $mg/m^2$/day.

9. The method of claim 8, wherein the dose of daunorubicin is between about 30 $mg/m^2$/day and about 150 $mg/m^2$/day.

10. The method of claim 9, wherein the dose of daunorubicin is about 60 $mg/m^2$/day.

11. The Method of claim 1, wherein the anthracycline is idarubicin administered at a dose between about 1 $mg/m^2$/day and about 25 $mg/m^2$/day.

12. The method of claim 11, wherein the dose of idarubicin is between about 3 $mg/m^2$/day and about 15 $mg/m^2$/day.

13. The method of claim 12, wherein the dose of idarubicin is about 12 $mg/m^2$/day.

14. The method of claim 1, wherein the dose of COMPOUND 2 is about 20 to 2000 mg/day.

15. The method of claim 1, wherein the dose of COMPOUND 2 is about 50 to 500 mg/day.

16. The method of claim 1, wherein the dose of COMPOUND 2 is about 50 mg/day.

17. The method of claim 1, wherein the dose of COMPOUND 2 is about 75 mg/day.

18. The method of claim 1, wherein the dose of COMPOUND 2 is about 100 mg/day.

19. The method of claim 1, wherein AML is selected from newly diagnosed AML, untreated AML, AML arising from myelodysplastic syndrome, AML arising from antecedent hematologic disorder and AML arising after exposure to genotoxic injury.

20. The method of claim 1 wherein the dose of COMPOUND 2 is about 500 mg/day.

21. The method of claim 1 wherein the induction regimen consists of cytarabine administered for 7 days and daunorubicin administered for 3 days.

22. The method of claim 1 wherein the induction regimen consists of cytarabine administered for 7 days and idarubicin administered for 3 days.

* * * * *